US010538818B2

(12) United States Patent
Van Sinderen et al.

(10) Patent No.: US 10,538,818 B2
(45) Date of Patent: Jan. 21, 2020

(54) **METHODS AND KITS TO DETERMINE THE SENSITIVITY OF STRAINS OF *LACTOCOCCUS LACTIS* BACTERIA TO PHAGE INFECTION**

(71) Applicant: DSM IP ASSETS B.V., Heerlen (NL)

(72) Inventors: Douwe Van Sinderen, Echt (NL); Finn Vogensen, Echt (NL); Jennifer Mahony, Echt (NL); Witold Kot, Echt (NL); Stuart Ainsworth, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 895 days.

(21) Appl. No.: 14/773,065

(22) PCT Filed: Mar. 13, 2014

(86) PCT No.: PCT/EP2014/055043
§ 371 (c)(1),
(2) Date: Sep. 4, 2015

(87) PCT Pub. No.: WO2014/140229
PCT Pub. Date: Sep. 18, 2014

(65) Prior Publication Data
US 2016/0017408 A1 Jan. 21, 2016

(30) Foreign Application Priority Data
Mar. 13, 2013 (EP) ..................................... 13158881

(51) Int. Cl.
*C12Q 1/689* (2018.01)
(52) U.S. Cl.
CPC ......... *C12Q 1/689* (2013.01); *C12Q 2600/16* (2013.01)
(58) Field of Classification Search
None
See application file for complete search history.

(56) References Cited

FOREIGN PATENT DOCUMENTS

| DE | 102004023188 A1 | 12/2005 | | |
|----|---|---|---|---|
| EP | 2238837 A1 | 10/2010 | | |
| WO | 0177334 A2 | 10/2001 | | |
| WO | WO-03045172 A1 * | 6/2003 | ............... | A23B 4/22 |
| WO | 2010049540 A1 | 6/2010 | | |

OTHER PUBLICATIONS

Settanni et al. Journal of Microbiological Methods 2007; 69: 1-22. (Year: 2007).*
Elnifro et al. Clinical Microbiology Reviews 2000; 13: 559-570. (Year: 2000).*
Mahony et al. Applied and Environmental Microbiology 2013; 79: 4385-4392. (Year: 2013).*
Frantzen et al. Applied and Environmental Microbiology 2018; 84: e02199-17 (Year: 2018).*
Machine translation of WO 2001/77334 A2. 67 pages. Obtained Dec. 21, 2018. (Year: 2018).*
GenPept Accession No. CAL96832.1 for possible surface protein [*Lactococcus lactis* subsp. *cremoris* MG1363]; Feb. 27, 2015 [online], [retrieved on Dec. 21, 2018], retrieved from the Internet: <URL: www.ncbi.nlm.nih.gov/protein/124491911>. (Year: 2015).*
Gao et al. Journal of Bacteriology 2011; 193: 2886-2887 (Year: 2011).*
GenPept Accession No. ADZ62858.1 for glycosyl transferase, group 2 family protein [*Lactococcus lactis* subsp. *lactis* CV56]; Feb. 10, 2015 [online], [retrieved on Dec. 21, 2018], retrieved from the Internet: <URL: www.ncbi.nlm.nih.gov/protein/ADZ62858.1?report=genpept&log$=seqview>. (Year: 2015).*
Kelly et al. Frontiers in Microbiology 2013; 4: 257 (9 pages). (Year: 2013).*
International Search Report from corresponding PCT/EP2014/055043, dated Aug. 6, 2014.
Dupont et al., "Identification of the Receptor-Binding Protein in 936-Species", Applied and Environmental Microbiology, Oct. 2004, vol. 70,. No. 10, pp. 5818-5824.
Dupont et al., "Identification of Lactococcus lactis Genes Required for Bacteriophage Adsorption", Applied and Environmental Microbiology, Oct. 2004, vol. 70, No. 10, pp. 5825-5832.
Johansen et al., "Development of quantitative PCR and metagenomics-based approaches for strain quantification of a defined mixed-strain starter culture", Systematic and Applied Microbiology Elsevier, vol. 37, 2014, pp. 186-193.
Mahony et al., "Investigation of the Relationship between Lactococcal Host Cell Wall Polysaccharide Genotype and 936 Phage Receptor Binding Protein Phylogeny", JournalsASM.org, Applied and Environmental Microbiology, pp. 4385-4392, Jul. 2013, vol. 79, No. 14.
Ndoye et al, "Exploring suppression subtractive hybridization (SSH) for discriminating *Lactococcus lactis* ssp. *cremoris* SK11 and ATCC 19257 in mixed culture based on the expression of strain-specific genes", Journal of Applied Microbiology, Journal of Applied Microbiology ISSN, pp. 499-512.
Veesler et al., "Structure of the phage TP901-1 1.8 MDa baseplate suggests an alternative host adhesion mechanism", pp. 8954-8958, PNAS, Jun. 5, 2012, vol. 109, No. 23.
Wegmann et al., "Complete Genome Sequence of the Prototype Lactic Acid Bacterium *Lactococcus lactis* subsp. *cremoris* MG1363", Journal of Bacteriology, Apr. 2007, vol. 189, No. 8, pp. 3256-3270.
Opposition letter to EP 2971088 (EP 14715554.3) dated Nov. 27, 2019.
Mahony, Jennifer et al., "Structural Aspects of the Interaction of Dairy Phages with Their Host Bacteria", Viruses, 2012, pp. 1410-1424, vol. 4.
Chapot-Chartier, Marie-Pierre et al., "Cell Surface of Lactococcus lactis Is Covered by a Protective Polysaccharide Pellicle", The Journal of Biological Chemistry, Apr. 2, 2010, pp. 10464-10471, vol. 285, No. 14.

(Continued)

*Primary Examiner* — Angela M. Bertagna
(74) *Attorney, Agent, or Firm* — MCBee Moore & Vanik IP, LLC

(57) ABSTRACT

A kit useful for determining the phage susceptibility of one or more strains of *Lactococcus lactis* is described. The disclosure also describes methods for formulation of mixed defined starter cultures using strains from different phage sensitivity groups.

15 Claims, 4 Drawing Sheets
Specification includes a Sequence Listing.

(56) References Cited

OTHER PUBLICATIONS

Ainsworth, Stuart et al., "Complete Genome of Lactococcus lactis subsp. cremoris UC509.9, Host for a Model Lactococcal P335 Bacteriophage", Genome Announcements, Jan.-Feb, 2013, vol. 1, No. 1.
Bolotin, Alexander et al., "The Complete Genome Sequence of the Lactic Acid Bacterium Lactococcus lactis ssp, lactis IL1403", Genome Research, 2001, pp. 731-753, Vol, 11.
Siezen, Roland J. et al,, "Complete Genome Sequence of Lactococcus lactis subsp. lactis KF147, a Plant-Associated Lactic Acid Bacterium", Journal of Bacteriology, May 2010, pp. 2649-2650, vol. 192, No. 10.
NCBI, "Lactococcus lactis subsp. cremoris SK11, complete genome", Host: National Center for Biotechnology Information, Mar. 29, 2017.
Edwards, Mary C. et al., "Multiplex PCR: Advantages, Development, and Applications", Genome Research, 1994, 565-575, vol. 3.
Notice of Opposition received in European Patent Application No. 1471554.3 dated Dec. 2, 2019.

\* cited by examiner

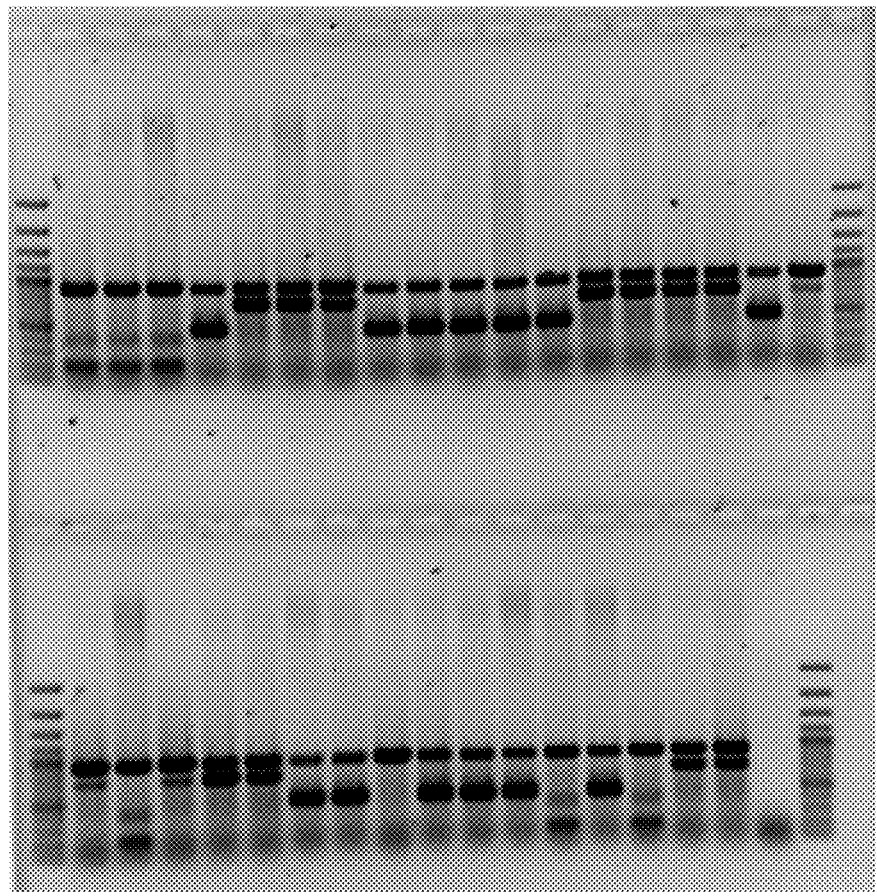
Fig. 2 (contd).

METHODS AND KITS TO DETERMINE THE SENSITIVITY OF STRAINS OF *LACTOCOCCUS LACTIS* BACTERIA TO PHAGE INFECTION

CROSS REFERENCE TO RELATED APPLICATIONS

This application is a § 371 National Stage Application of PCT/EP2014/055043, filed 13 Mar. 2014, which claims priority to EP 13158881.6, filed 13 Mar. 2013.

BACKGROUND

Field of the Invention

The present invention relates generally to kits and methods for determining the sensitivity of bacteria, especially strains of *Lactococcus lactis*, to phage, particularly phages belonging to the so-called 936 and P335 species.

Description of Related Art

In cheese-making, the single most important cause of fermentation failures is caused by bacteriophage infection of the starter culture(s) used. The dairy fermentation industry employs a lot of preventative measures such as starter strain selection and rotation. Traditionally, starter strain classification was performed through the application of phenotypic analysis using, for example, arginine hydrolysis, salt and thermal tolerance. Such analyses are time-consuming and expensive if applied in large scale screens.

It is an object of the invention to overcome at least one of the above-referenced problems.

SUMMARY

The invention relates to kits and methods for determining the sensitivity of bacteria, especially strains of *Lactococcus lactis*, to phage, particularly phages belonging to the so-called 936 and P335 species. The methods and kits of the invention are based on the discovery that a particular gene cluster/operon, designated here as cwps, which encodes the biosynthetic machinery for the manufacture of the so-called pellicle or cell wall polysaccharide (CWPS) of strains of *L. lactis*, contains regions that can function as a diagnostic variable of the phage sensitivity of the strain and a tool to determine the phage sensitivity of the strain. Thus, the sensitivity of a strain of *Lactococcus lactis* to phage, especially phages of the 936 or P335 species, can be determined by analysing the gene content of the cwps operon of the strain to determine the phage sensitivity profile of the strain. In particular, the Applicant has identified three cwps-associated regions that can be used to classify strains into four major phage-related groups having varying phage-sensitivity profiles, and developed multiplex PCR for classifying strains into one of these four phage-related groups. The methods of the invention are therefore based on determining the sensitivity of bacteria to phage, determining whether a mix of starter strains comprises a phage sensitive strain, determining the composite phage sensitivity profile of a mix of starter strains and formulation mixed defined starter cultures that are composed of strains from some or all of the different phage-relates groups.

Accordingly, in a first aspect, the invention relates to a kit useful for determining the phage susceptibility of one or more strains of *Lactococcus lactis* by means of polymerase chain reaction (PCR), ideally multiplex PCR, comprising:

(a) a first primer pair adapted to generate a first amplicon correlating to a region of the cwps operon that is unique to a particular group of *L. lactis* strains, among which MG1363 and SK11, referred to here as the MG-SK type strains;

(b) a second primer pair adapted to generate a second amplicon correlating to a region of the cwps operon that is unique to a particular group of *L. lactis* strains, among which IL1403 and KF147, referred to here as the IL-KF type strains;

(c) a third primer pair adapted to generate a third amplicon correlating to a region of the cwps operon that is unique to a particular group of *L. lactis* strains, among which UC509.9 and CV56, referred to here as the UC-CV type strains; and (d) optionally, a control primer pair adapted to amplify a sequence conserved in strains of *L. lactis*.

DETAILED DESCRIPTION OF A PREFERRED EMBODIMENT

Figure 1:
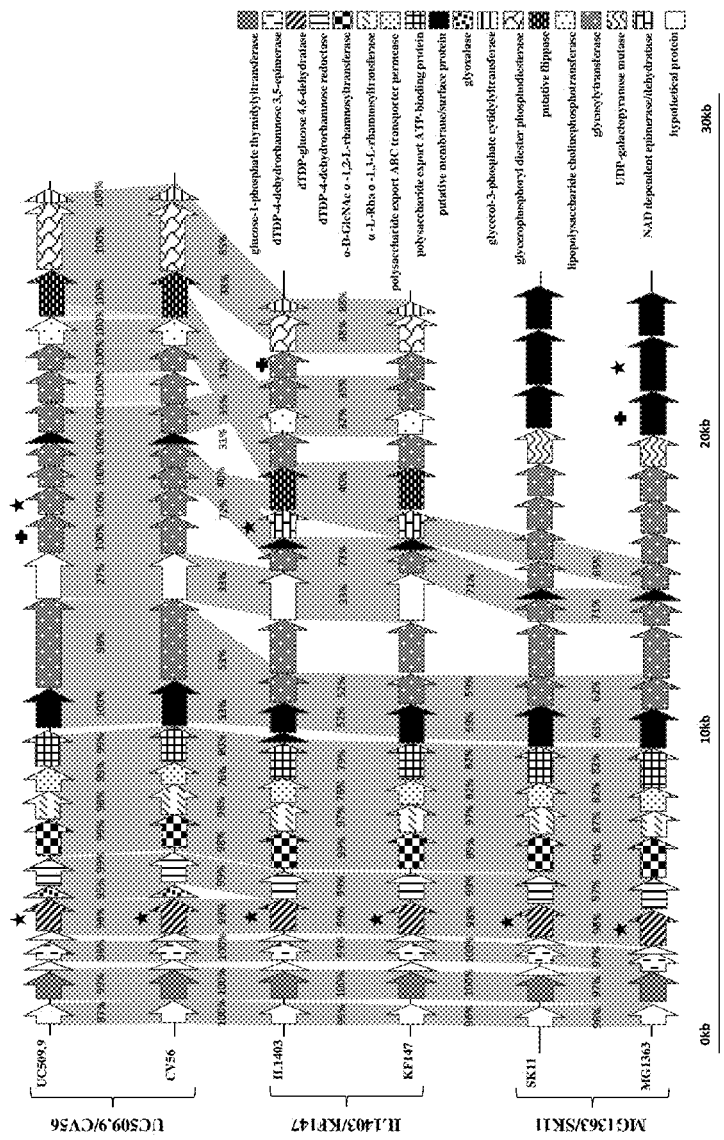
FIGS. 1-3 depict embodiments of the disclosure described herein.

Thus, the four phage-related groups of *L lactis* are MG-SK type strains, IL-KF type strains, UC-CV type strains, and strains that are not part of any of the above three groups.

Typically, the first primer pair is adapted to generate an amplicon comprising or consisting of a sequence of SEQUENCE ID NO: 9. Suitably, the first primer pair comprises a forward primer comprising or consisting of the sequence of SEQUENCE ID NO: 1 and a reverse primer comprising or consisting of the sequence of SEQUENCE ID NO: 2.

Typically, the second primer pair is adapted to generate an amplicon comprising or consisting of a sequence of SEQUENCE ID NO: 10. Suitably, the second primer pair comprises a forward primer comprising or consisting of the sequence of SEQUENCE ID NO: 3 and a reverse primer comprising or consisting of the sequence of SEQUENCE ID NO: 4.

Typically, the third primer pair is adapted to generate an amplicon comprising or consisting of a sequence of SEQUENCE ID NO: 11. Suitably, the third primer pair comprises a forward primer comprising or consisting of the sequence of SEQUENCE ID NO: 5 and a reverse primer comprising or consisting of the sequence of SEQUENCE ID NO: 6.

Preferably, in the kit of the invention: (a) the first primer pair comprises a forward primer comprising the sequence of SEQUENCE ID NO: 1 and a reverse primer comprising the sequence of SEQUENCE ID NO: 2; (b) the second primer pair comprises the sequence of SEQUENCE ID NO: 3 and a reverse primer comprising the sequence of SEQUENCE ID NO: 4; and (c) the third primer pair comprises the sequence of SEQUENCE ID NO: 5 and a reverse primer comprising the sequence of SEQUENCE ID NO: 6.

Typically, the conserved sequence comprises all or part of the rmlB gene. Ideally, the control primer pair is adapted to generate an amplicon comprising or consisting of a sequence of SEQUENCE ID NO: 12. Ideally, the control primer pair comprises a forward primer comprising or consisting of the sequence of SEQUENCE ID NO: 7 and a reverse primer comprising or consisting of the sequence of SEQUENCE ID NO: 8.

Preferably, the kit comprises at least two further primer pairs, namely a first further primer pair adapted to generate an amplicon selected from one of SEQUENCE ID NO'S 26 to 30 (for example SEQUENCE ID NO: 26), and a second further primer pair adapted to generate an amplicon selected from another of SEQUENCE ID NO'S 26 to 30 (for example, SEQUENCE ID NO: 27). These further primer pairs may be employed to sub-type bacteria identified as belonging to the MG-SK strain type.

Typically, the kit comprises, 3, 4 or 5 further primer pairs, each of which is adapted to generate a different amplicon selected from SEQUENCE ID NO'S 26 to 30.

The invention also relates to a kit useful for determining the phage susceptibility of one or more strains of *Lactococcus lactis* by means of polymerase chain reaction (PCR), ideally multiplex PCR, comprising:
  (a) a first primer pair adapted to generate a first amplicon from a region of the cwps operon that is unique to a particular group of *L. lactis* strains, among which MG1363 and SK11, referred to here as the MG-SK type strains;
  (b) a first further primer pair adapted to generate an amplicon selected from one of SEQUENCE ID NO'S 26 to 30;
  (c) a second further primer pair adapted to generate an amplicon selected from another of SEQUENCE ID NO'S 26 to 30; and
  (d) optionally, a control primer pair adapted to amplify a sequence conserved in strains of *L. lactis*.

Typically, the kit comprises, 3, 4 or 5 further primer pairs, each of which is adapted to generate a different amplicon selected from SEQUENCE ID NO'S 26 to 30.

The invention also relates to a method for classifying a strain of *Lactococcus lactis* according to phage sensitivity, comprising the steps of:
  (i) providing a sample comprising at least one strain of *Lactococcus lactis*;
  (ii) performing a PCR analysis of the sample using at least a first primer pair adapted to generate a test amplicon correlating to a region of the cwps operon that is a biomarker of phage sensitivity profile and, optionally, a control primer pair adapted to generate a second amplicon correlating to a region of the cwps operon that is conserved amongst strains of *Lactococcus lactis*; and
  (iii) correlating the presence or absence of the test amplicon with phage sensitivity profile of the strain of *L. lactis*.

The test amplicon may be, for example, a biomarker of phage sensitivity, phage insensitivity, or intermediate phage sensitivity. Examples of such biomarkers are SEQUENCE ID NOs: 9 to 11 which are regions of the cwps operon on *L. lactis* strains that correlate with phage sensitivity, intermediate phage sensitivity, and phage insensitivity, respectively. The level of sensitivity referred to here relates to the finding that (a) *L. lactis* strains of the MG-SK cwps type were observed to be sensitive to more phages than strains possessing the IL-KF or UC-CV cwps type in this study (phage sensitive), (b) *L. lactis* strains of the UC-CV cwps type were not sensitive to any phages in this study (phage insensitive), while (c) *L. lactis* strains possessing the IL-KF cwps type were infected by an intermediate number of phages in this study (intermediate phage sensitivity), and these may be representative of Lactococcal strains applied in the dairy industry and in culture collections. Other biomarkers include the sequences of SEQUENCE ID NOs 13, 14 & 15 relating to strains of the MG-SK (phage sensitive), IL-KF (intermediate phage sensitivity) and the UC-CV (phage insensitive) cwps types, respectively.

Suitably, the method for classifying a strain of *Lactococcus lactis* according to phage sensitivity comprises the steps of:
  (i) providing a sample comprising at least one strain of *Lactococcus lactis*;
  (ii) performing a multiplex PCR analysis of the sample using
    (a) a first primer pair adapted to generate a first amplicon correlating to a region of the cwps operon that is a biomarker of phage sensitivity (*L. lactis* strains that belong to the so-called MG-SK type);
    (b) a second primer pair adapted to generate a second amplicon correlating to a region of the cwps operon that is a biomarker of intermediate phage sensitivity (*L. lactis* strains that belong to the so-called IL-KF type);
    (c) a third primer pair adapted to generate a third amplicon correlating to a region of the cwps operon that is a biomarker of phage insensitivity (*L. lactis* strains that belong to the so-called UC-CV type); and
    (d) optionally, a control primer pair adapted to amplify a sequence conserved in *L. lactis*; and
  (iii) correlating the presence or absence of the amplicons with phage sensitivity profile of the strain of *L. lactis*.

Preferably, the method for classifying a strain of *Lactococcus lactis* according to phage sensitivity, comprises the steps of:
  (i) providing a sample comprising at least one strain of *Lactococcus lactis*;
  (ii) performing a multiplex PCR analysis of the sample using
    (a) a first primer pair adapted to generate a first amplicon correlating to a region of the cwps operon that is unique to *L. lactis* strains MG1363 and SK11 (*L. lactis* strains that belong to the so-called MG-SK type);
    (b) a second primer pair adapted to generate a second amplicon correlating to a region of the cwps operon that is unique to *L. lactis* strains IL1403 and KF147 (*L. lactis* strains that belong to the so-called IL-KF type);
    (c) a third primer pair adapted to generate a third amplicon correlating to a region of the cwps operon that is unique to *L. lactis* strains UC509.9 and CV56 (*L. lactis* strains that belong to the so-called UC-CV type); and
    (d) optionally, a control primer pair adapted to amplify a sequence conserved in *L. lactis*; and
  (iii) classifying at least one strain according to phage sensitivity, wherein the presence of the first amplicon indicates the presence of a strain that is phage sensitive, the presence of the third amplicon indicates the presence of a strain that is phage insensitive, and the presence of the second amplicon indicates the presence of a strain having intermediate phage sensitivity.

Preferably, the method comprises an additional step of sub-typing strains identified as having a specific phage sensitivity profile according to phage sensitivity. Thus, for example, a strain or strains identified as being phage sensitive (or MG-SK strain type), phage insensitive (or UC-CV strain type), or intermediate phage sensitivity (or IL-KF strain type), can be sub-typed and further classified according to phage sensitivity.

Typically, phages identified as phage sensitive or MG-SK strain type, are sub-typed using one or more primer pairs adapted to generate an amplicon selected from SEQUENCE ID NO's 26 to 30, and sub-classified according to phage sensitivity according to the presence or absence of each amplicon.

Preferably, the phages are sub-typed using primer pairs adapted to generate one amplicon selected from SEQUENCE ID NO's 26 to 30.

The invention also relates to a method for determining the composite phage sensitivity of a mix of *Lactococcus lactis* strains, comprising the steps of:
(i) providing a sample comprising a mix of *Lactococcus lactis* strains;
(ii) performing a multiplex PCR analysis of the sample using
  (a) a first primer pair adapted to generate a first amplicon correlating to a region of the cwps operon that is unique to *L. lactis* strains MG1363 and SK11;
  (b) a second primer pair adapted to generate a second amplicon correlating to a region of the cwps operon that is unique to *L. lactis* strains IL1403 and KF147;
  (c) a third primer pair adapted to generate a third amplicon correlating to a region of the cwps operon that is unique to *L. lactis* strains UC509.9 and CV56; and
  (d) optionally, a control primer pair adapted to amplify a sequence conserved in *L. lactis*
wherein the PCR analysis provides a plurality of amplicons of different sizes; and
(iii) correlating the level of the first, second or third amplicons with phage sensitivity, wherein the first amplicon is indicative of phage sensitivity, the third amplicon is indicative of phage insensitivity, and the second amplicon is indicative of intermediate phage sensitivity.

Examples of the first amplicon include the sequences of SEQUENCE ID NO: 9 & 13.

Examples of the second amplicon include the sequences of SEQUENCE ID NO: 10 & 14.

Examples of the third amplicon include the sequences of SEQUENCE ID NO: 11 & 15.

Typically, the first primer pair is adapted to generate an amplicon comprising or consisting of a sequence of SEQUENCE ID NO: 9. Suitably, the first primer pair comprises a forward primer comprising or consisting of the sequence of SEQUENCE ID NO: 1 and a reverse primer comprising or consisting of the sequence of SEQUENCE ID NO: 2.

Typically, the second primer pair is adapted to generate an amplicon comprising or consisting of a sequence of SEQUENCE ID NO: 10. Suitably, the second primer pair comprises a forward primer comprising or consisting of the sequence of SEQUENCE ID NO: 3 and a reverse primer comprising or consisting of the sequence of SEQUENCE ID NO: 4.

Typically, the third primer pair is adapted to generate an amplicon comprising or consisting of a sequence of SEQUENCE ID NO: 11. Suitably, the third primer pair comprises a forward primer comprising or consisting of the sequence of SEQUENCE ID NO: 5 and a reverse primer comprising or consisting of the sequence of SEQUENCE ID NO: 6.

Typically, the conserved sequence comprises all or part of the rmlB gene. Ideally, the control primer pair is adapted to generate an amplicon comprising or consisting of a sequence of SEQUENCE ID NO: 12. Ideally, the control primer pair comprises a forward primer comprising or consisting of the sequence of SEQUENCE ID NO: 7 and a reverse primer comprising or consisting of the sequence of SEQUENCE ID NO: 8.

Preferably, the methods of the invention employ: (a) a first primer pair comprising a forward primer comprising the sequence of SEQUENCE ID NO: 1 and a reverse primer comprising the sequence of SEQUENCE ID NO: 2; (b) a second primer pair comprising the sequence of SEQUENCE ID NO: 3 and a reverse primer comprising the sequence of SEQUENCE ID NO: 4; (c) a third primer pair comprising the sequence of SEQUENCE ID NO: 5 and a reverse primer comprising the sequence of SEQUENCE ID NO: 6; and, optionally, (d) a control primer pair comprising a forward primer comprising or consisting of the sequence of SEQUENCE ID NO: 7 and a reverse primer comprising or consisting of the sequence of SEQUENCE ID NO: 8.

Suitably, the PCR conditions are about 95° C. for about 6 minutes followed by about 31 cycles of about 95° C. for about 15 seconds, about 57° C. for about 30 seconds, and about 72° C. for about 1 minute and a final extension step at about 72° C. for about 7 minutes. The term "about" should be understand to mean+/−5%.

The invention also relates to the use of a region of the cwps operon of a strain of *Lactococcus lactis* as a biomarker of phage sensitivity, ideally 936-type phage sensitivity, wherein the region is selected from the group consisting of:
a region unique among the reference strains to *L. lactis* strains MG1363 and SK11;
a region unique among the reference strains to *L. lactis* strains IL1403 and KF147;
and a region unique among the reference strains to *L. lactis* strains UC509.9 and CV56.

The term "unique" or "unique region" means a region of the cwps operon of a *L. lactis* strain that is found in both of the reference strains and not found in the other four reference strains of *L. lactis*. Thus, a region unique to *L. lactis* strains MG1363 and SK11 is a region of the cwps operon that is found in both strains MG1363 and SK11 but not found in any of *L. lactis* strains IL1403, KF147, UC509.9 and SK11. Thus, a strain of *L. lactis* that is found to have a region of the cwps operon that is unique to *L. lactis* strains MG1363 and SK11 can be classed as part of the MG-SK group of strains (phage sensitive strains). Likewise, a strain of *L. lactis* that is found to have a region of the cwps operon that is unique to *L. lactis* strains UC509.9 and CV56 can be classed as part of the UC-CV group of strains (phage insensitive strains). The region is generally of sufficient length to be detected by PCR, including multiplex PCR.

The term "phage sensitive" as applied to a strain of *L. lactis* should be understood to mean a strain belonging to the MG-SK type that is sensitive to infection by phage, typically infection by 936-type phage or P335 group phage The term "phage insensitive" as applied to a strain of *L. lactis* should be understood to mean a strain belonging to the UC-CV type that is highly insensitive to infection by phage, typically infection by 936-type phage or P335 group phage The term "intermediate phage sensitive" as applied to a strain of *L. lactis* should be understood to mean a strain belonging to the IL-KF type that exhibits a sensitivity to infection by phage, typically infection by 936-type phage or P335 group phage, that is intermediate the sensitivity of phage sensitive and phage insensitive strains.

Thus, for example, the invention also relates to the use of a region of the cwps operon of a strain of *L. lactis* that is unique to *L. lactis* strains MG1363 and SK11, for example SEQUENCE ID NO: 9, as a biomarker of phage sensitivity in strains of bacteria, especially strains of *Lactococcus lactis*. The invention also relates to the use of a region of the cwps operon of a strain of *L. lactis* that is unique to *L. lactis* strains UC509.9 and CV56, for example SEQUENCE ID NO:11, as a biomarker of phage insensitivity in strains of bacteria, especially strains of *Lactococcus lactis*. The invention also relates to the use of a region of the cwps operon of a strain of *L. lactis* that is unique to *L. lactis* strains IL1403 and KF147, for example SEQUENCE ID NO: 10, as a biomarker of intermediate phage sensitivity in strains of bacteria, especially strains of *Lactococcus lactis*.

The term "composite phage sensitivity" should be understood to mean the phage sensitivity of the starter mix.

The term "phage" as employed herein preferably means phages belonging to the 936 and/or P335 species. The term "936-type phage" means strictly lytic phage, having a well conserved genome organisation in three clusters; early, middle and late expressed regions (9). The term P335 group phage means phages that may be lytic or temperate and having a general genome arrangement of a lysogenic module (if the phage is a temperate one) oriented back-to-back with the replication module and proceeded by the structural module (25).

The invention also relates to the use of a region of the cwps operon of a strain of *Lactococcus lactis* as a biomarker of phage sensitivity.

The invention also relates to the use of a region of the cwps operon of a MG-SK type strain of *Lactococcus lactis* as a biomarker of phage sensitivity, ideally P335 or 936-type phage sensitivity, wherein the region is selected from the group consisting of SEQUENCE ID NO'S 26 to 30.

The invention also relates to a mixed defined starter culture comprising a plurality of *Lactococcus lactis* strains and comprising a first bacterial strain selected from one of an MG-SK type strain, a UC-CV type strain, and an IL-KF type strain, and a second bacterial strain selected from another of an MG-SK type strain, a UC-CV type strain, and an IL-KF type strain. Examples of combinations include a MG-SK type strain plus a UC-CV type strain, or a MG-SK type strain plus an IL-KF type strain, or a UC-CV type strain plus an IL-KF type strain.

The term "defined" means that the strains in the mixed starter culture have been identified as being different strains.

Typically, the mixed starter culture comprises an MG-SK type strain, a UC-CV type strain, and an IL-KF type strain. Examples of mixed starter cultures according to the invention include:

*L. lactis* IL1403 (IL-KF), WM1 (UC-CV) and 3107 (MG-SK); or *L. lactis* F7/2 (IL-KF), C10 (UC-CV) and FD13 (MG-SK).

The term "mixed starter culture" as used herein should be understood to mean a mixture of cultures or a combination of cultures provided in the form of a kit in which the different cultures are not mixed together.

The invention also relates to a mixed starter culture comprising a plurality of *Lactococcus lactis* strains of the MG-SK strain type, and comprising a first bacterial strain selected from one of a $C_1$ to $C_5$ sub-type, and a second bacterial strain selected from another of a $C_1$ to $C_5$ sub-type. Examples of combinations include a $C_1$ plus $C_2$ type strain, or a $C_2$ plus $C_5$ type strain. CWPS sequences that characterise the $C_1$ to $C_5$ sub-types are provided below in Table 6, and primer pairs for use in identification of the sub-types using PCR are provided in Table 5.

The invention also relates to a method of formulating a mixed starter culture comprising the steps of classifying a plurality of strains of *Lactococcus lactis* according to phage sensitivity according to a method described above to identify a plurality of strains having differing phage sensitivity, and formulating a mixed starter culture using the plurality of strains having differing phage sensitivity.

Typically, the mixed starter culture is formulated into a single composition comprising a mixture of cultures or a kit comprising the plurality of cultures stored separately.

The kits, methods and uses of the invention may be employed to determine or characterise the sensitivity of bacteria, especially *L. lactis* bacteria, to phage, especially P335 and 936 phage.

FIG. 1. Comparison of the genomic regions encoding the cwps biosynthesis cluster of six lactococcal strains (UC509.9, CV56, IL1403, KF147, SK11 and MG1363). Homologous protein-encoding genes are joined by grey blocks including the level of identity (aa %). The three sub-groups of cwps are the UC-CV, the IL-KF and the MG-SK sub-groups with unique regions highlighted in the operons of UC509.9, IL1403 and MG1363 in the schematic by stars to indicate the genes upon which the multiplex PCRs are based. The control for the multiplex PCR was based on rmlB, which is conserved in each of the strains. The genes upon which alternative primer sets could be designed are indicated by a black plus sign above the relevant genes, which may be used as alternative biomarkers.

Figure 2:
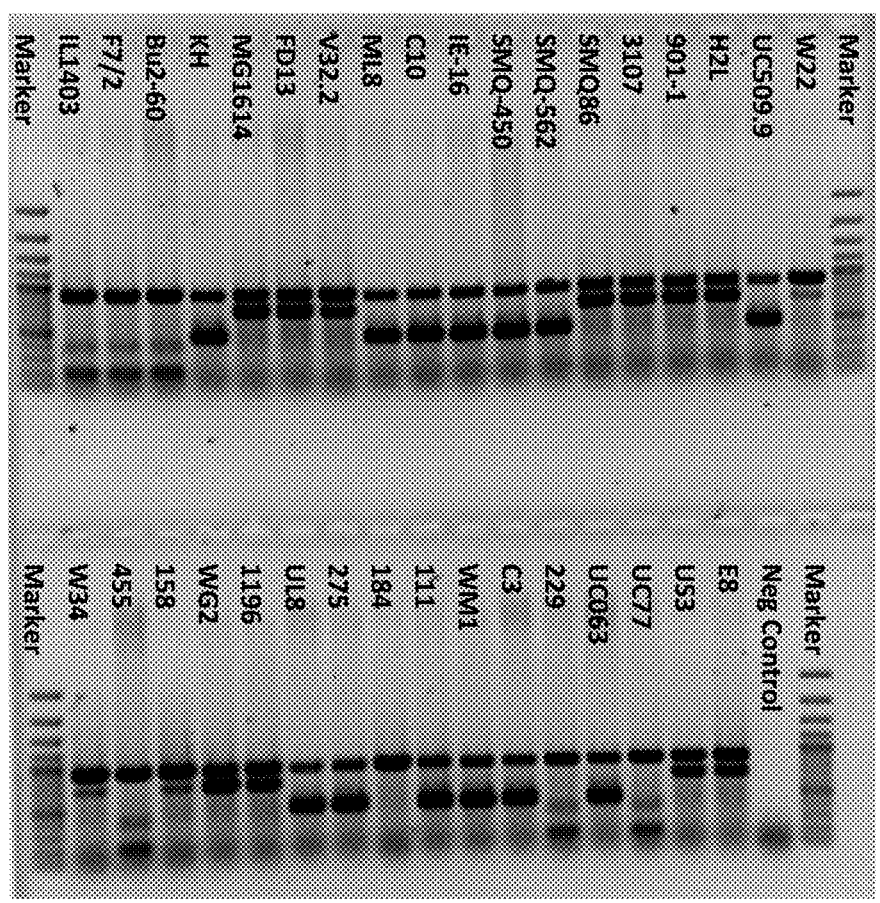

FIG. 2: Multiplex PCR for the detection of conserved (control) regions and differential regions of the CWPS cluster of lactococcal genomes. Strains IL1403 (IL-KF CWPS), MG1614 (MG-SK CWPS) and UC509.9 (UC-CV CWPS) are the controls for each CWPS type tested for in this assay. A negative control was also included without template DNA in the reaction. The control band is observed in all cases with differential amplicons observed for each of the assessed strains with the exception of 184, which does not belong to any of the three known CWPS types.

Figure 3:
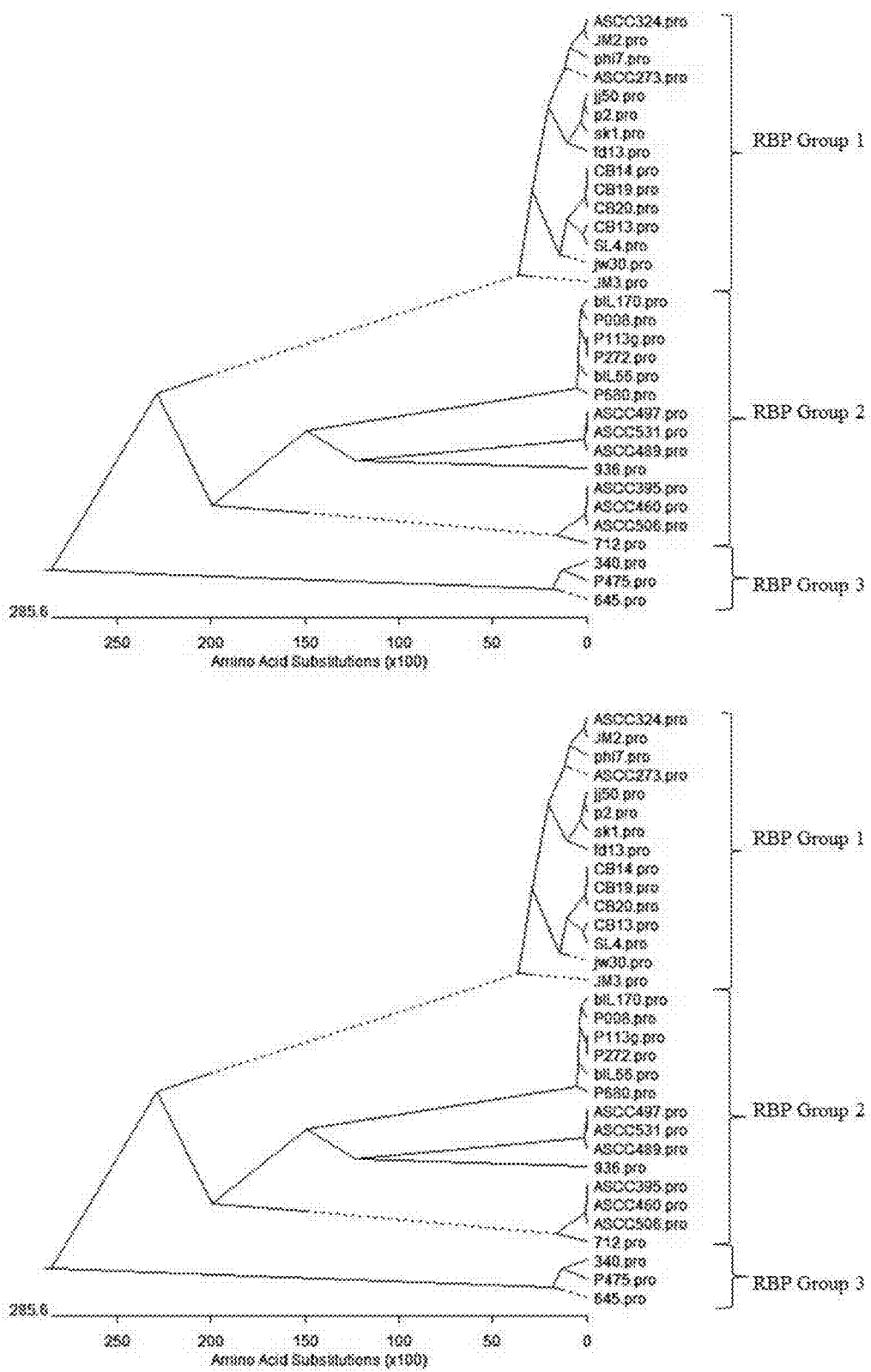

FIG. 3. Above is a representative phylogenetic tree of the RBP variable C-termini of thirty 936 phages including the eleven sequenced phages of this study. Three major groups of the 936 RBPs are observed: Group 1 includes the majority of phages in this study that infect strains with a MG-SK CWPS (except 936), Group 2 includes those phages in this study that infect strains with an IL-KF CWPS while Group 3 represents a small group with a divergent RBP that predominantly infect strains with an IL-KF CWPS but also infect a strain with the MG-SK CWPS with equal efficiency.

Materials & Methods

Lactococcal Strains and Bacteriophages

Lactococcal strains (Table 1) were grown in M17 broth supplemented with 0.5% glucose at 30° C. without agitation. Phages were propagated on the relevant strains at 30° C. in M17 broth (Oxoid) supplemented with 0.5% glucose without agitation as previously described (18). The phages used in this study and relevant details are listed in Table 1. Plaque assays were performed using the double agar method as previously described (15). This method was also applied for the host range analysis performed against a bank of lactococcal strains (Table 1). Frequency of lysogeny assays using the erythromycin-tagged phage TP901erm (a derivative of TP901-1, also designated as TP901-BC1034) was performed as previously described (4).

Phage Purification & DNA Preparation

Phage purification by Caesium chloride gradient was performed as previously described (22). The generated purified phage suspension (1 ml) was precipitated with 10% polyethylene glycol 8000 (Sigma-Aldrich) and 0.5 M sodium chloride at 4° C. overnight. Subsequently, the suspension was centrifuged at 17,700 g for 15 minutes and the supernatant removed. Alternatively, phage suspension was dialyzed as described for phage 2. The PEG/salt-induced precipitate was resuspended in 0.5 ml of TE buffer (pH 9.0) and treated with 20 µl of 20 mg·ml$^{-1}$ proteinase K for 20 minutes at 56° C. followed by treatment with SDS at a final concentration of 2% at 65° C. for 20 minutes. This mixture was then phenol/chloroform (25:24:1 phenol:chloroform: isoamyl alcohol, Sigma Aldrich) treated at least twice and the aqueous phase precipitated with 2.5 volumes of ice cold 96% ethanol and 0.1 volume of sodium acetate (pH 4.8). Subsequent to centrifugation, the pellet was washed in 70% ethanol and resuspended in 100 µl of TE buffer (pH 8.0).

Genome sequencing, assembly & annotation

5 µg of DNA of phages 645, 340, ViridusJM2 (JM2), PastusJM3 (JM3) and PI 13g was extracted and verified by nanodrop quantification and confirmatory molecular ID tests were conducted on the DNA extract prior to shipment to the contract sequencing facility (Macrogen Inc., Korea). A 40- to 65-fold sequencing coverage was obtained using pyrosequencing technology on a 454 FLX instrument. The files generated by the 454 FLX instrument were assembled with GS assembler (454, Branford, Conn.) to generate a consensus sequence. Phages P475, fd13, cp7, 936, P272 were sequenced using the 454 Roche Titanium platform. These phages were sequenced as part of tagged pools of unrelated phages, built as MID-tagged Rapid libraries and sequenced in one region (half a picotitre plate) using the GS FLX Titanium Sequencing Kit XLR70. One phage, P680, was sequenced as 96 base reads using the Illumina HighSeq2000 platform, again as part of a pool of unrelated phages, tagged with an index as part of one lane of the flowcell. Custom indexing primers were used to build libraries as described earlier (12). Reads were assembled into contigs using CLC Genomics Workbench 5.0.1 (CLC bio, Aarhus, Denmark). Quality improvement of the genome sequence involved sequencing of 15-25 PCR products across the entire genomes to ensure correct assembly, double stranding and the resolution of any remaining base-conflicts occurring within homopolynucleotide tracts. Protein-encoding open reading frames (ORFs) were predicted using Zcurve_V and Genmark.hmm followed by manual assessment and, where necessary, correction. A preliminary identification and functional annotation of ORFs was performed on the basis of BLASTP analysis against the non-redundant protein database (nr) provided by the National Centre for Biotechnology Information.

Phage Accession Numbers

The Genbank accession numbers for the phages sequenced in this study are as follows: 340 KC182542; 645 KC182543; 936 KC182544; fd13 KC182545; JM2 KC182546; JM3 KC182547; P113G KC182548; P272 KC182549; P475 KC182550; P680 KC182551; φ7 KC182552.

CWPS-Typing of Lactococcal Strains by Multiplex PCR

The relevant DNA regions encompassing the cell wall polysaccharide biosynthesis operon in the sequenced lactococcal strains IL1403 (accession number: AE005176), KF147 (accession number: NC_013656.1), MG1363 (accession number: NC_009004.1), SK11 (accession number: NC_008527.1), UC509.9 (accession number: CP003157.1) and CV56 (accession number: CP002365.1) were analysed and compared using BLASTP analysis as described above. Using this data conserved and unique regions within the operons of these strains were identified (FIG. 1). Primers were designed based on LLKF_205 of IL-KF (Product=183 bp), llmg_0226 of MG-SK (Product=686 bp) and UC509_0206 of UC-CV CWPS (Product size=442 bp) types as indicated in FIG. 1 (Tables 3 and 4). A control was also included in which primers based on the conserved gene rmlB were used to generate a product of 891 bp to verify that the reaction was working in all samples. The multiplex PCR included these four sets of primers and was applied to the strains assessed in the host range analysis (Table 1) under the following conditions: 95° C. for 6 minutes followed by 31 cycles of 95° C. for 15 seconds, 57° C. for 30 seconds and 72° C. for 1 minute and a final extension step at 72° C. for 7 minutes.

Electron Microscopy

A drop of the purified phage suspension was applied to a Formvar-carbon-coated copper grid for 5 min, then removed with a pipette and immediately replaced with 3% (vol/vol) uranyl acetate. After 1 min, the liquid was removed with a filter paper. The grids were examined in a Philips CM12 transmission electron microscope at 80 kV.

Cloning

All recombinant plasmids (Table 1) were generated in *Escherichia coli* Top10 (Invitrogen, USA). All primers, except where stated, were ordered from Eurofins MWG (Ebersberg, Germany). The variable section (i.e. variable within C type strains) of the CWPS biosynthesis gene cluster of *L. lactis* 3107, encompassing genes 3107_003 to 3107_006, was amplified using KOD DNA polymerase (Invitrogen, USA) and cloned into the low copy number, nisin-inducible vector pPTPi. Plasmid constructs were then transformed into the *L. lactis* MG1363 nisRK-containing derivative *L. lactis* NZ9000, in which plasmid pJP005 (27) had been introduced to allow recombineering and nisin-inducible expression.

Recombineering and Oligonucleotides

Recombineering was performed in *L. lactis* NZ9000 or derivatives thereof as previously described (27), with associated modifications as optimized for *L. lactis* and executing a given transformation with 500 µg of a particular oligonucleotide, which in some cases contained phosphorothioate linkages (Integrated DNA Technologies, Leuven, Belgium).

Bioinformatic Analyses

For comparative analysis of the CWPS biosynthesis gene clusters that belong to the MG-SK type, as identified by multiplex PCR, relevant genomic regions encompassing the CWPS biosynthesis gene cluster from lactococcal strains MG1363 (accession number: NC_009004.1), SK11 (accession number: NC_008527.1) and IO-1 (accession number: AP012281) were employed. The full genome analyses of *L. lactis* strains 3107, W34, JM1, JM2 and JM3 are currently in progress and these results will be published elsewhere. The genomic regions responsible for CWPS biosynthesisin the latter five strains were identified based on BLASTN analysis against the reference CWPS biosynthesis gene cluster of *L. lactis* MG1363 and submitted to GenBank under the following accession numbers; *L. lactis* 3107 (KF498848), *L. lactis* W34 (KF498852), *L. lactis* JM1 (KF498849), *L. lactis* JM2 (KF498850) and *L. lactis* JM3 (KF498851). The presumed CWPS region of each genome was analysed and compared in detail using BLASTP and Interpro analysis. Using the genomic data corresponding to the CWPS biosynthesis region of the above mentioned strains, conserved and variable regions were identified.

Results

Selection of Phages for this Study

Eleven phages were selected for this study in order to assess genome diversity among the 936 phages. The phages represent a broad range of 936 phages isolated across Europe (and one New Zealand phage) during a time period that spanned the 1980s until 2010 (Table 1). Firstly, phages that have been applied in many studies of 936 phage-host interaction studies over the past decades such as P680, P113g, P272 and 645 were selected. Secondly, phage 936 was selected to serve as the prototype member of the 936 phage species for comparative purposes. Furthermore, its geographical location of isolation was a consideration as the remainder of the phages are of European background (Table 1). Finally, the geographical origin and year of isolation of the selected phages was considered, and therefore phages that had been isolated over the past thirty years in Ireland (ViridusJM2 and PastusJM3), Germany (P680, P113g, P272) and Denmark (fd13, 645, 340, ϕ7, P475) and New Zealand (936) were selected.

Host Range Analysis

Thirty four lactococcal strains (Table 1) were assessed for their sensitivity to the eleven phages sequenced in this study. All phages assessed in this study have a relatively narrow host range and are limited to infecting at most six different strains from this panel of thirty four possible hosts. It is also noteworthy that host range convergence was observed for certain members of the sequenced group of phages. For example, 645 and 340 have a similar host range as do P272 and P113g (Table 2). Since these phages are derived from similar geographical locations, it is perhaps unsurprising that these apparent sub-groups of phages possess related host ranges. Viridus JM2, Pastus JM3, fd13 and 936 display very narrow host specificities infecting only a single strain among those tested.

Multiplex PCR CWPS Strain Typing

BlastP analysis of the CWPS clusters of the sequenced lactococcal strains identified three major CWPS subgroups based on conserved sequences, allowing classification into the MG-SK, IL-KF and UC-CV CWPS subgroups (FIG. 1). Each subgroup is defined by unique regions that were used to develop a multiplex PCR-based typing method (see Materials and Methods section). This was applied to classify the CWPS type of each of the strains used in this study. Of the 34 strains assessed, six strains were in this way classified as the IL-KF CWPS-type, fourteen belonged to the MG-SK CWPS-type, while thirteen belonged to the UC-CV CWPS-type. One strain (L. lactis subsp. lactis 184) did not generate an amplicon for any of the three CWPS types although the conserved region present in all three subtypes was amplified (FIG. 2), which may be indicative of an as yet unidentified CWPS type not represented by the three sub-types presented in this study.

Correlation of CWPS Type & Host Range

Of the eleven phages, five phages (fd13, 936, ϕ7, ViridusJM2 and PastusJM3) are largely limited to infecting strains of the MG-SK CWPS type (Table 2). Conversely, the remaining six phages are almost completely limited to infecting hosts with the IL-KF CWPS type. There are exceptions to this generalisation, however, such as phages 645 and 340 which were shown to infect L. lactis subsp. cremoris 3107 (MG-SK cwps) as well as L. lactis subsp. lactis IL1403 (IL-KF cwps) and four other strains of this cwps type. These phages can infect strains of both cwps types with a relative efficiency. The same is true for phage P475, which infects strains of the IL-KF cwps type, but which also infects L. lactis W22 (MG-SK cwps) however at a much lower efficiency (EOP=$10^{-6/7}$). Interestingly, none of the strains possessing the UC-CV cwps-type were infected by any of the 936-type phages assessed in this study.

Correlation of RBP Group & Host Range

The RBPs of the sequenced phages were used to perform a comparative sequence analysis which also included sequences of previously sequenced 936 phage RBPs. Since the amino-terminal regions of these proteins are well conserved, the first 130 residues were removed from the RBP sequences and a comparison of the much more variable sequences of the RBPs carboxy-terminus was performed. Through this analysis, three sub-groups of RBP are identifiable (FIG. 3): Group 1 corresponds to what was previously termed the sk1-like or L. lactis subsp. cremoris-infecting phages (17); Group 2 contains the bIL170-like or L. lactis subsp. lactis-infecting phages (17); while Group 3 represents a distinct but small group of phages that infect primarily L. lactis subsp. lactis strains, but are also capable of infecting strains of L. lactis subsp. cremoris (Table 2). While there are three main RBP groups, subtle sub-groups within these groups can be distinguished (FIG. 2). The phages in this study of the RBP group 1 exclusively infect strains that possess the MG-SK CWPS type. Similarly, the majority of phages in this study of RBP group 2 infect strains that possess the IL-KF-type CWPS, while those belonging to group 3 appear to preferentially infect strains of the IL-KF CWPS type, though they are occasionally also capable of infecting strains with a MG-SK-type CWPS as mentioned above (the cases of P475, 645 and 340).

Sub-Typing of CWPS Type MG-SK Strains

As determined, three variations of a particular genetic locus present in L. lactis strains, termed the UC-CV, IL-KF, and MG-SK types, can be linked to RBP phylogeny of 936 phages. To determine if additional genetic diversity within the CWPS biosynthesis gene cluster of a given CWPS type exists, we analysed the genetic locus encompassing the presumed CWPS biosynthetic operon of eight lactococcal genomes (three publicly available genomes and the CWPS regions of five strains from our own collection), all belonging to the MG-SK type (as first determined by PCR). This comparative sequence analysis revealed the presence of a variable region within these examined CWPS MG-SK type loci, allowing the identification of five subtypes among members of the MG-SK type (designated subtype $C_1$ to $C_5$) based on differences/similarities within this variable region within the various type MG-SK CWPS biosynthesis loci. Primers for generating the $C_1$ to $C_5$ subtype are provided in Table 5 and the generated amplicons are provided in Table 6.

Primers were designed based on the unique regions of each of the 5 sub-types and can be applied in a multiplex PCR approach to perform CWPS MG-SK sub-typing of lactococcal strains (Table 5). The sequence differences between subtypes suggest that $C_2$ to $C_5$ subtype strains produce structurally different CWPS compared to the previously determined $C_1$ type structure of L. lactis MG1363 (5). The sub-typing of lactococcal strains of the CWPS MG-SK type permits a deeper insight into the specific relationships between phages and these strains and elucidates the components that phages of the 936 or P335 species recognise and specifically target. For example, the lactococcal P335 phages LC3 and TP901-1 cannot infect L. lactis NZ9000, which possesses the CWPS $C_1$ sub-type. Conversely, these phages can infect another lactococcal strain named 3107, which possesses CWPS $C_2$ sub-type.

Genetic Swapping of the Variable Region of the CWPS of a MG-SK Subtype Strain Causes a Change in Phage Sensitivities to Both 936 and P335 Type Phages Due to the high level (99-100%) of DNA sequence identity observed across conserved regions of the CWPS biosynthesis gene clusters found in the $C_1$ subtype strain L. lactis MG1363 and the C2 subtype strain L. lactis 3107, it was reasoned that if the variable genes found in the C2 subtype CWPS biosynthesis locus of *L. lactis* 3017 were to be supplied in trans to the *L. lactis* MG1363 NICE expression system derivative *L. lactis* NZ9000 ($C_1$ subtype), carrying a mutation in one of its variable CWPS genes, the resulting recombinant strain would produce the structural equivalent of *L. lactis* 3107 CWPS (which is of the $C_2$ subtype), thus effectively causing change of CWPS subtype by this genetic swapping. To test this hypothesis, the variable region of the $C_2$ subtype CWPS biosynthesis gene cluster was first cloned from *L. lactis* 3107 (i.e. genes 3107_003, 3107_004 and 3107_005) into the nisininducible plasmid pPTPi, thereby generating plasmid pPTPiC2. The latter plasmid was then introduced into *L. lactis* NZ9000-GT1, an NZ9000 derivative in which gene LLNZ_01145, which is one of the genes of the variable region within the native CWPS biosynthesis MG-SK type gene cluster, had been mutated by recombineering. This mutant carries an in-frame TGA stop codon in LLNZ_01145, which in turn causes the resulting mutant, designated NZ9000-GT1, to display a phage-resistant (to phages belonging to the 936 species) and sedimenting phenotypes (data not shown), all being consistent with the expected loss of CWPS biosynthesis. Introduction of plasmid pPTPiC2 and induced expression of the variable region of the $C_2$ subtype CWPS biosynthesis gene cluster from *L. lactis* 3107 on this plasmid *L. lactis* in NZ9000-GT1 restored wild type non-sedimenting cell growth, indicating the production of a functional CWPS of subtype $C_2$.

To determine if the presumed $C_2$ subtype CWPS produced in *L. lactis* NZ9000-GT1 pPTPiC2 functions as a bacteriophage-host cell surface receptor, the induced strain was challenged by plaque assay with various P335 species phages (Table 7), whose primary indicator strain is *L. lactis* 3107. Of the phages tested, only the P335 species phage ϕLC3, which is unable to form plaques on WT *L. lactis* NZ9000 or un-induced NZ9000-GT1 pPTPiC2, was able to infect and form plaques on induced NZ9000-GT1 pPTPiC2 at an EOP of $10^{-1}$ and can be propagated to levels of $10^7$-$10^8$ pfu/ml (data not shown). This clearly demonstrates that the CWPS of *L. lactis* 3107 is the host cell-surface receptor of the P335 species phage ϕLC3, and that this CWPS, when produced in NZ9000, is sufficient for this strain to become susceptible to ϕLC3 infection. Interestingly, another P335 species phage, TP901erm, which also uses *L. lactis* 3107 as a host, was not able to form plaques on induced NZ9000-GT1 pPTPiC2. However, the frequency of lysogeny of TP901erm on induced *L. lactis* NZ9000-GT1 pPTPiC2 increases $10^4$ fold compared to *L. lactis* NZ9000-GT1 pPTPi (TP901erm can lysogenize *L. lactis* NZ9000 at a very low frequency ($10^{-8}$)), reaching levels similar to those observed for *L. lactis* 3107 ($10^{-4}$), thus showing that CWPS from 3107 is also the cell surface receptor for of the P335 species phage TP901erm.

TABLE 1

Features of the lactococcal strains and phages used in this study

| Strain | Source/Reference | *L. lactis* subspecies | CWPS type | Phage infected |
|---|---|---|---|---|
| IL1403 | (1) | lactis | IL-KF | + |
| F7/2 | (24) | lactis biovar *diacetylactis* | IL-KF | + |
| Bu2-60 | (19) | lactis biovar *diacetylactis* | IL-KF | + |
| 455 | | cremoris | IL-KF | + |
| UC77 | UCC | cremoris | IL-KF | + |
| 229 | UCC | lactis | IL-KF | − |
| WM1 | UCC | lactis | UC-CV | − |
| ML8 | (6) | cremoris | UC-CV | − |
| C10 | UCC | cremoris | UC-CV | − |
| IE-16 | (6) | cremoris | UC-CV | − |
| SMQ-450 | (6) | cremoris | UC-CV | − |
| SMQ-562 | (6) | cremoris | UC-CV | − |
| 111 | (6) | cremoris | UC-CV | − |
| UC063 | UCC | cremoris | UC-CV | − |
| UC509.9 | UCC | cremoris | UC-CV | − |
| UL8 | UCC | lactis | UC-CV | − |
| 275 | UCC | lactis | UC-CV | − |
| KH | (23) | cremoris | UC-CV | − |
| C3 | (10) | cremoris | UC-CV | − |
| W22 | (21) | cremoris | MG-SK | + |
| W34 | (11) | cremoris | MG-SK | + |
| 3107 | (3) | cremoris | MG-SK | + |
| WG2 | (24) | cremoris | MG-SK | + |
| FD13 | (7) | cremoris | MG-SK | + |
| H2L | (2) | cremoris | MG-SK | + |
| 158 | (9) | cremoris | MG-SK | + |
| V32.2 | (7) | cremoris | MG-SK | + |
| JM3 | UCC | cremoris | MG-SK | + |
| JM2 | UCC | cremoris | MG-SK | + |
| SMQ86 | (6) | cremoris | MG-SK | − |
| US3 | | cremoris | MG-SK | − |
| E8 | | cremoris | MG-SK | − |
| MG1614 | (8) | cremoris | MG-SK | − |
| 901-1 | (3) | cremoris | MG-SK | − |
| 184 | UCC | lactis | unknown | − |

| Phage | Source location | Year of first report/isolation | Propagating host | Genome length (kb) | G + C % | No. orfs | RBP-group |
|---|---|---|---|---|---|---|---|
| fd13 | Denmark | 2004 | FD13 | 30.674 | 34.7 | 53 | 1 |
| P113g | Germany | 1986 | IL1403 | 30.796 | 34.1 | 58 | 2 |

TABLE 1-continued

Features of the lactococcal strains and phages used in this study

| P272 | Germany | 1986 | IL1403 | 30.778 | 34.1 | 61 | 2 |
| 936 | NZ | 1984 | 158 | 27.302 | 34.5 | 49 | 2 |
| P475 | Europe | Unknown | 455 | 30.961 | 34.3 | 57 | 3 |
| P680 | Germany | 2009 | IL1403 | 29.631 | 35.1 | 49 | 2 |
| φ7 | Denmark | 2004 | V32.2 | 32.382 | 34.2 | 57 | 1 |
| 645 | Denmark | 2004 | IL1403 | 29.247 | 35.0 | 51 | 3 |
| 340 | Denmark | 2010 | IL1403 | 32.337 | 34.5 | 58 | 3 |
| ViridusJM2 | Ireland | 2010 | JM2 | 31.090 | 34.3 | 59 | 1 |
| PastusJM3 | Ireland | 2010 | JM3 | 28.674 | 34.4 | 52 | 1 |

TABLE 2

Host range of phages assessed in this study

| Strain | subspecies | CWPS | P680 | P113g | P272 | P475 | 645 | 340 | Φ7 | fd13 | 936 | Viridus JM2 | Pastus JM3 |
|---|---|---|---|---|---|---|---|---|---|---|---|---|---|
| IL1403 | lactis | IL-KF | + | + | + | + | + | + | | | | | |
| F7/2 | lactis | IL-KF | + | | | | + | + | | | | | |
| Bu2-60 | lactis | IL-KF | + | + | + | + | + | + | | | | | |
| UC77 | cremoris | IL-KF | | | | | + | + | | | | | |
| 455 | cremoris | IL-KF | | | | + | + | + | | | | | |
| 3107 | cremoris | MG-SK | | | | | + | + | | | | + | |
| V32.2 | cremoris | MG-SK | | | | | | | + | | | | |
| FD13 | cremoris | MG-SK | | | | | | | | + | | | |
| W22 | cremoris | MG-SK | | | + | | | + | | | | | |
| W34 | cremoris | MG-SK | | | | | | + | | | | | |
| 158 | cremoris | MG-SK | | | | | | + | | | + | | |
| 1196 | cremoris | MG-SK | | | | | | + | | | | | |
| US3 | cremoris | MG-SK | | | | | | | | | | | |
| E8 | cremoris | MG-SK | | | | | | + | | | | | |
| JM2 | cremoris | MG-SK | | | | | | | | | | + | |
| JM3 | cremoris | MG-SK | | | | | | | | | | | + |

TABLE 3

Primers for CWPS multiplex PCR

| Primer name | Sequence (5'-3') | Product size (bp) |
|---|---|---|
| MG-SKfw | AAAGCTCATCTTTCCCCTGTTGT (SEQ ID NO: 1) | |
| MG-SKrv | GCACCATAGTCTGGAATAAGACC (SEQ ID NO: 2) | 686 |
| IL-KFfw | GATTCAGTTGCACGGCCG (SEQ ID NO: 3) | |
| IL-KFrv | AGTAAGGGGGCGGATTGTG (SEQ ID NO: 4) | 183 |
| UC-CVfw | GTGCCTATGCTCCGTTAGTC (SEQ ID NO: 5) | |
| UC-CVrv | CGAGGGCCAATCTCTTTACC (SEQ ID NO: 6) | 442 |
| CONfw | GTACACTATGTTTATAACAATCATCCAG (SEQ ID NO: 7) | (Control) |
| CONrv | GCAAACCAGATTCAAAGTCAGTATG (SEQ ID NO: 8) | 891 |

TABLE 4

Amplicon (product) sequences

MG-SK
AAAGCTCATCTTTCCCCTGTTGTCTATGTAAACAATGTATCAATTCAACA
AGGAACAAGTACGAATACTACAAAAATGAATGTTCCAATTAAGGCTTTCA
ACTCCCCAGACAATAATTTTGGAATGACGGCGAATGTGATTTCTCAGACA
ACTGGAACTCAGATTACCTCGTCTGCTCCCAAAGTGAATACGACTGGTAT
AAATTTTGTTGAAGTGGATGCAAATAAAAATAAGATGGTTAGAGATGCTG
TTTATATTTTAGGGAAGAATGTGGGTGGTAAAAAGTATCTATATGATAGT
CAAGGGAAATGGAGCGAAATTCAAGATTTGTCTACAGTTTCTCCTACAAG
CTATACTTTATTAAGAGGTGGGAACCAATATGTTTTTGGTGATGATGATG
TATCTCCAATTGAGTTGAATAATACAAGATTCAATTATGATTATGAACGT
GATACCAAAATTAATCAATCTTTAATCAAATTATTTGGTTTGGGAGAAGG
AAAAGATTATTTCCTTTATCAGGTTGCCGCTCCTACTAACTACTCTGTTG
ATAAAACACCCATTGATTTTTCTATTTTTTCAGAAAATGTAGTTTCGCCT
AATGGTAGCCAACTTACTAAAACTAGTATGAAGACAGCAAGCAACCAATC
ATTTAAACTAAATGGTCTTATTCCAGACTATGGTGC
(SEQ ID NO: 9)

IL-KF
GATTCAGTTGCACGGCCGTATGAAACTCATCAAGTTAATTTTGATAGTAC
GATGACACTTCTCGAGATCTTACGTCAAAATAAAAAATCATTGAAACGAT
TTGTTTTTTCTTCAAGCGCAGCAGTTTATGGTGATGAGCCAACACTTCCT
AAGCAGGAAGAGGGCACAATCCGCCCCCTTACT (SEQ ID NO: 10)

UC-CV
GTGCCTATGCTCCGTTAGTCTTTGATCATGAAATCCAAATTTCCCCAACA
GCAAGTGATACATTGAAAATGATTAATTTTCCTAAAAAACCAGGAATTTA
TTCTGAAAATCTAACTGGGATTTCAAGTTGTCTGGTTGTAAAGAGCGACT
TATTAATAGAAATTGGCGACTGAATATTGAATTTCCCTTAGATTATCTT
GACCATTGGCTATTTTGGAAAATTTTTAATTCTAATAAAAAGGTAGTAGT
AATTAATGAAAAATAAATCACCATCTTTCTATTCAAGAAATAAATCAAA
CAAATGATCTGAGATTTTATAGTATCTTCTCTAGTGAATATCATTTTTAT

TABLE 4-continued

Amplicon (product) sequences

AAGTATTATAAGCCGGAATTGCTCTTAAATCTTTATAAAAAATATGTTAG
AATGATTATTAAAGGAATTCTTGGTAAAGAGATTGGCCCTCG
(SEQ ID NO: 11)

CON
GTACACTATGTTTATAACAATCATCCAGACGTGCATATCACAGTTTTGGA
TAAATTAACTTATGCAGGAAATGTTAATAACATTAACATGTTATTTGACA
GTGGACGTGTCGAACTTGTTGTTGGCGACATTGCAGACCCTGAAATTGTT
GATCAAGTGGCTTCTAAAGCAGATGCAATTGTTCACTATGCAGCTGAGAG
CCATAATGATAATTCATTGAAATCTCAAGATGAATTTATACAAACAAACT
TTATCGGAACTTATACGTTGATTCAAGCGGCTCGTAAATATGATTTACGT
TTCCACCATGTTTCTACTGATGAAGTTTATGGTGATTTGCCTTATCGCGA
AGATTTGCCAGGCCATGGCGAAGGTGAAGGTGAAAAATTTACTGACAAAA
CACCTTACAATCCATCAAGCCCCTACTCTTCAACTAAAGCGGCTTCTGAT
TTAATTGTTGCTTGGGTACGTTCATTTGGACTTAAAGCAACAATTTC
AAACTGCTCAAATAACTACGGACCTTTTCAACACATCGAAAAATTTATTC
CTCGTCAAATTACTAATATTCTTTCAGGAATCAAACCAAAACTTTACGGT
GATGGTAAAAACGTTCGAGACTGGATTCATACAGACGACCATTCATCAGG
CGTTTGGACAATTTTGATAAAAGGTCGTATGGGTGAACTTACCTTATCG
GTGCAGACGGTGAAAAAAATAACAAAGAAGTTCTTGAAGATATTTTGACT
CGTATGGGCAAAGATAAGAGCGATTATGATCGTGTAACTGACCGTGCTGG
CCATGACCTTCGGTACGCAATTGACAATACAAAATTGCGTACCGAACTTG
GTTGGGCTCCAAAACATACTGACTTTGAATCTGGTTTGC
(SEQ ID NO: 12)

MG-SK
ttgaaagtattaaaaaactatcttctgaatagctcttaccaattattgatt
gtgattattccaattatcacgattccttatatttctagggtgcttggcaca
acggctataggtttaaatacatttacctatgcaattattcagtactttgta
ttagctggttcaattgggataacaacttatggaaatcgagagattgcatat
catcaatctgataaagaaaagagaagccaaatttttcgggaaatttcattt
ttgagattttgtaccattgctctctctttctctatttttctgtattttctta
gcctttcaaaaacaggattttgagatttatctcttgcagagtatcgctatt
atcgctgcggctttgatatttcttggtatttttatgggagtggaaaatttc
aagcgaacagtagggcgtaatttattgtctctattatttcagttatttc
atctttactttttattaaggatgtcaaaggatttgcccattatgttttcatta
attactggaacatcattgattggaaatcttcactttggccatatttgcgc
aaggaaattttcgctcccaaatggaaagaattagcattaggacatcattta
aaacccacactattactttttttgccgcaaattgctacacagatttataca
attgcaaacaaaacgatgatttttgatgggaaaacggcatcggga
ttttttagtcaatcggatagtctgattaaagtaacattgagcattgtcact
tattaggtgtagtcatgagcctcatgatcaaatcattacaaaaggtaaat
taaagaagttcaagagactttaaaaaaatcatcgtccttatgactgggctt
gctgtaccgataatgatggcgttatgggaatagcactcaattagcaggatt
ctattcggccctaaatgggtagctgttggtcctttgctaatgatggaagcc
ccaattattatattcattgcttggagtaatgtttgggaattcagtaccttt
cttccattaaatcggatgagagaattcacaacttcggtaacaattggtgca
gttcttaatattttacttaattttgctttgattcctcttttggggctcact TABLE 4-continued Amplicon (product) sequences ggtgcaatgattgcgacagtaattgccgaggcttcagtgacgatttatcaa
ttttatattttgagaaatgactttgagataattccaatgatgattttatcttgc
tggaaatacttttttatctggtgcagtgatgtgtttggagctgttttctattta
aacaattcttttgaagatgaatatgcataatcttatatttcaagtattgatt
ggtgctataatatatataaattcttaatatcttattgaaatccagtcttttt
attgaagtcaaaaagattgtaagtaaaaatttaa
(SEQ. ID. NO. 13).

IL-KF
atgataacaaagagtaacatactaataacaggtggagcaggttttattggc
tcaagtttagcgaacgaattactacctcaaaataagattactgttattgat
aatctttcgatgggagattttaataatcttcatgaaacaagtaatcttaca
aaaattttaggtgatgtcactgataaaaatctcctggtaaaagttttggaa
gaaaatgattagattatattatcattagcagcaattgcttcggagccgat
tcagagcacggccgtatgaaactcatcaagttaattagatagtacgatgac
acttctcgagatcttacgtcaaaataaaaaatcattgaaacgatttgtttt
ttcttcaagcgcagcagtttatggtgatgagccaacacttcctaagcagga
agagggcacaatccgcccccttactccttatgcaattgataaatttgcatc
tgaaaaaatgacaatgattttataatatttatatgatgttcctaccagtgc
aacacgcttttttcaatgtttatggaccaaatcaaaatcccagttcaccta
ttcaggatttattttccattcttgttgaccgtttgcgagaaaatacagaatt
gactattttttggagatggagaacagtctcgagattttgtatatatagaaga
tgttattcaagcattattactaatagcgacctctgaacaatcctttgaga
agtctataatgtcgggactggggtcaaaaattcaataaacgatttaacgaa
atttgctcaaaaatttacaaataaagagttatctatcaaatttgatgatgt
gcgacaaggagatatcaaagactcagtttccgatattcaaaacttaagga
cataggatactcacctaaatttgatttatctaatggtatgaagaagtatct
caactacgagtttaaataa (SEQ. ID. NO. 14).

UC-CV
atgaatttaacaatttgcttagtagcttatagtcaaaaatttacagagaca
gtctcattttattctttattaaacttgactaagaatctaaaagtaaaatatt
aatttatatatattgacaatggaagtgaagattatcgtcctctcatgagga
gaggatactcattcatttcatagcttgaactatatttataataaacaaaaa
gaacgtggtactagaattgcttatcaaagtatatagatgttagtcaagatg
aatggttaatgatttagacgatgatacagaaaatttcacaaccatatttatc
gaaaatttatcagaaataaaaaaaagaaaaccaaagtgatatttgtgccta
tgctccgttagtctttgatcatgaaatccaaatttcccccaacagcaagtga
tacattgaaaatgattaattacctaaaaaaaccaggaatttattctgaaaat
ctaactgggattcaagagtctggagtaaagagcgacttattaataagaat
tggcggactgaatattgaatttccttagattatcttgaccattggctatt
ttggaaaattttaattctaataaaaggtagtagtaattaatgaaaaat
aaatcaccatctttctattcaagaaataaatcaaacaaatgatctgagatt
ttatagtacttctctagtgaatatcattttataagtattaagcgga
attgctcttaaatctttataaaaaatatgttagaatgattattaaaggga
tcttggtaaagagattggccctcgttggaaaattttattaaaaatattatt
ggagagaaaatga (SEQ. ID. NO. 15).

TABLE 5

Primers used in the sub-classification of the MG-SK CWPS type lactcococcal strains (C1 to C5)

| Primer name | Primer sequence (5'-3') | SEQ ID | Expected amplicon size (bp) |
|---|---|---|---|
| C1fw | gtcatcaaacatactttcgtc | 16 | 650 |
| C1rv | aagttttgccattgtttctcc | 17 | |
| C2fw | gaacaatggattatttatgctga | 18 | 450 |
| C2rv | attcccattttcagcaacaag | 19 | |
| C3fw | gttgtaattgttactagccag | 20 | 250 |
| C3rv | tcaatcgcattatagattacacc | 21 | |
| C4fw | gattttattcgaggcttagca | 22 | 968 |
| C4rv | tagcattacaatcaatctgtca | 23 | |

TABLE 5-continued

Primers used in the sub-classification of the
MG-SK CWPS type lactcococcal strains (C1 to C5)

| Primer name | Primer sequence (5'-3') | SEQ ID | Expected amplicon size (bp) |
|---|---|---|---|
| CSfw | gattatattcggggcttagca | 24 | 1141 |
| CSrv | tgtaatatggtattgtctagca | 25 | |

TABLE 6

Sub-typing amplicon (product) sequences $C_1$
gtcatcaaacatactttcgtcatatgtgcgtatatgcaatctccgtatttagaggaaagtataaaatcaattttag
accaaggatctattaaagaaggaaatcagaagtggttttatatacttctactcctaatgattatatagaaaatatt
tgtcataaatataatatcaaaatatttattggtgaaggtggaggcattggagcagattggaatggagctttagcgg
cagttcaaactaaatatgctacaattgttcatcaagacgatctatatgataagaaatatggagaaatgataattaa
tgattttgagtctcaaaaagactctaatattgtttttactgactattatgaaattgatgaatactctaaacctaga
aaaagaaatattaatttaaaaataaaaagtttaggattaaaactaatgtcttttgggaaaataaaaaatatcaaa
gaagagtttactcttttggtaatttatttgttgcccagctgttcttataatatggaacgtcttaaagattttag
atttaatgaagagatgaaaatggcggtagactgggatgcatgggaaagaataatgaaaaaatctggacatgtccat
tatcttccgctaaaattgatggctcatagaatacatagtgattcggaaacaaccaataatactttaaataaaaaca
gagaaaaagaagagcacgagatgtttcgaagatattgggagaaacaatggcaaaactt [SEQ ID NO. 26]

$C_2$
gaacaatggattatttatgctgaaaaattaaagcaaatgtttcctgaaatgaaattaatagggtggctgcatctgg
atctcaaccattatgaaacttatcatcttgcgaaaagcaaaaatcaatttttaaatggtcttagggtgtgtgatcg
gttgattgtactaactcaagaggaaaaaaatgttctagaaaaccgcggatttgaaaaagttcaagtttttgcataat
ccacttacattaaatgatacaaataaagttgtggacttgaataaaaaaataatatcatgggtaggacggattgata
ttagcataagggcaggactatttaatagagatagcgaaaattagcctgacgactgggaaattagagtagctggacc
ggaagggacaacaaaagatttaaaaaattgattgaaaaaaataggcttacgaataaaaattttatgggtaggtccga
aaaatggagaagaactaacatatcattatttaaatagctccaattataatgacatcaagatttgaaagctaggctt
agtattggtagaagcaatgaactatggtatcctataattgcattctcacaaacaggaagtgatgaaattcttaaaa
atgaacaatatggccttgttgctgaaaatgggaat [SEQ ID NO. 27]

$C_3$
gttgtaattgttactagccagcatgataaagacttgcctactaaagaagaatttgatcatttgaaaatatatcggt
tgcctattagaaagatttggaaaaatcggtatccttttccattaaaaaatgaaagatataaacaattaatttctga
tattacttctgaaccaattgactattatgtagtgaatacaagatttcaattgcctgctttattaggtgcccagtta
gcaaaaaagcaggaaaagaagccttggtattagagcatgggaccacgtacctcacattaaataattctttgttag
atagcatacttcacaggatagagcacttttggttaaaaaaatcaaaaaaaatactaagactttttacggtgtttc
aaaagaagctactgaatggttaaagacttttggaatagaggctaaaggtgtaatctataatgcgattga
[SEQ ID NO. 28]

$C_4$
gattaattcgaggcttagcaaagaaaatataacatagaaagagtattatataaatgagtgaaaagaaatatgattc
ggagactaggaacgacttcaagagatactacgaatgatgttagcagattttgataaaatatgctaagataacgata
ttgattattttttaatgggtggaagtttacttggagctgtaaggcacaatgggatgatacctgggatgatgatat
tgacgttggaatgactggtgagaattatgataaaatttatacaagtcatgaataattcacaaaaatgaaaaatatagt
cttatgagtagtgagagcgaggaaagctataccactcagattgtactggatattttagcatttgacaatctagcag
ataatgaaagacgtgcaaaaattcaaggtataaaatctttcatatatgggaaactttcatatcttacaacaattga
aaaccctacagttcatcaagtaggaataaaactattttttattaatactacaataaaaagtcttcaaaaaacatt
caaacttttttaaagttaccccctaaattttttattaaaaaaggtgaaggagtagctagaaaatataactcttctcaa
acgcaaagagtaatgtatatgaatcagtcaaaaatgattcagaaatattgatcgaaatgacctcttaccaactaga
cgtgagattagatggacaaaaaataaaaattccaaaggaaacagataaatatttggctgcacattatggtgattat
atgacacttccaccagaagataaaagatataatcattatacggccattttagattttggaaagtataaataaggta
aaatataatgaaagataaagaaaaaattgtattggttgctggaacttttgatattttgcatgagagccacgttaat
atgttgaaaaatgctaaaaatcttggtgacagattgattgtaatgcta [SEQ ID NO. 29]

$C_5$
gattatattcggggcttagcaaagaaaattttaacatagaaagagtattttttataaatgagtgaaaagaaatatga
ttcggagactttagaaggacttcaagagatactacgaatgatgttagcagattttgataaaatatgcgaagataac
gatattgattattttttagtaggtggaagtttacttggagcgataaggcacaatgggatgataccttgggatgatg
acattgacattggtatgaccggaaaagattatgataaaatttattcaaatcatgaagaagagggaatctgataaata
tacgcttataagtagtgaaacaaataaagaattccatatttgcgatctgcgggatttatgctaaatggtacaaaa
tttataaaagatatttcaataatggatgaaacctcttctagtatagtagttgacattattgcgttcgataacttag
cagatggtaagttaaaaagcatctcacaaggcttaaaaacatttttctacggtaaatctgccaccttacaactctg
aataatcctacgaatcataggaaaggaatttcaaaaattgttacgacagttatgataaaaatgctccatggattat
ttaagttatttaaagtaaccccacatactcattaacaaaggaaacaaaatagcaacgaaatataatatgctggaa
acaggaagagtcatgtacatgaatgaatctaaaccgtattagttacaattaagaagaaaaatttatacccataaag
aaaattccattgatggcttgatgattagtgtcccaaaataacccagaacagtatttattagaaagatatggagatta
taagacactaccgccagaaagtgagcaatataatcatttcccagatgtattggactttggagaatacaaaaattta
aggagaagagagcaatgaaattagcattattgacggctgaggagttggtagccgtatgaaacaagaggtacctaa

TABLE 6-continued

Sub-typing amplicon (product) sequences acagtttattcatgtaaatgataaacctttaatcatttatgctttagaggcttttcaaaagcatccagatattgat
gtaattgctattgcatgcttagaaggatggaaaaatgttttggaggcatatgctagacaataccatattaca
[SEQ ID NO. 30]

TABLE 7

Strains, plasmids and bacteriophage used in sub-typing examples

| Strains, plasmids or phage | Relevant features | Reference/source |
| --- | --- | --- |
| Bacterial strains | | |
| Lactococcus lactis subsp. cremoris NZ9000 | L. Lactis MG1363 derivative containing nisRK. Host to sk1 | (14) |
| Lactococcus lactis subsp. cremoris 3107 | Host to φLC3, TP901-1E, ViridusJM2 and JW31 | (3) |
| Lactococcus lactis subsp. cremoris NZ9700 | Nisin producing L. lactis strain | (14) |
| Lactococcus lactis subsp. cremoris NZ9000-GT1 | NZ9000 with GAATTC insert in LLNZ_0045, resulting in an in-frame TGA stop codon | This work |
| Lactococcus lactis subsp. cremoris NZ9000-GT2 | NZ9000 with GAATTC insert in LLNZ_0050, resulting in an in-frame TGA stop codon | This work |
| Escherichia coli One Shot ® TOP10 | F⁻ mcrA Δ (mrr-hsdRMS-mcrBC) Φ80lacZ ΔM15 ΔlacX74 recA1 araΔ139 Δ (ara-leu)7697 galU galK rpsL (Str$^r$) endA1 nupG | Invitrogen, USA |
| Plasmids | | |
| pJP005 | pNZ8048 containing recA | (26, 27) |
| pPTPi | E. coli-L. lactis shuttle vector, PnisA, Tet$^r$ | (20) |
| pPTPiC2 | pPTPi containing genes 3107_003, 3107_4 and 3107_5 | This work |
| Bacteriophages | | |
| φLC3 | P335 species, propagated on 3107 | (16) |
| TP901erm | P335 species, Em$^r$, propagated on 3107 | (13) |

The invention is not limited to the embodiment hereinbefore described which may be varied in construction and detail without departing from the spirit of the invention.

REFERENCES

1. Bolotin, A., P. Wincker, S. Mauger, O. Jaillon, K. Malarme, J. Weissenbach, S. D. Ehrlich, and A. Sorokin. 2001. The complete genome sequence of the lactic acid bacterium *Lactococcus lactis* s sp. *lactis* IL1403. Genome research 11:731-753.
2. Boyce, J. D., B. E. Davidson, and A. J. Hillier. 1995. Spontaneous Deletion Mutants of the *Lactococcus lactis* Temperate Bacteriophage Bk5-T and Localization of the Bk5-T attP Site. Applied and environmental microbiology 61:4105-4109.
3. Braun, V., S. Hertwig, H. Neve, A. Geis, and M. Teuber. 1989. Taxonomic Differentiation of Bacteriophages of *Lactococcus lactis* by Electron Microscopy, DNA-DNA Hybridization, and Protein Profiles. J Gen Microbiol 135:2551-2560.
4. Breum, S. O., H. Neve, K. J. Heller, and F. K. Vogensen. 2007. Temperate phages TP901-1 and phi LC3, belonging to the P335 species, apparently use different pathways for DNA injection in *Lactococcus lactis* subsp. *cremoris* 3107. Fems Microbiol Lett 276:156-164.
5. Chapot-Chartier, M. P., E. Vinogradov, I. Sadovskaya, G. Andre, M. Y. Mistou, P. Trieu-Cuot, S. Furlan, E. Bidnenko, P. Courtin, C. Pechoux, P. Hols, Y. F. Dufrene, and S. Kulakauskas. 2010. Cell surface of *Lactococcus lactis* is covered by a protective polysaccharide pellicle. The Journal of biological chemistry 285:10464-10471.
6. Deveau, H., S. J. Labrie, M. C. Chopin, and S. Moineau. 2006. Biodiversity and classification of lactococcal phages. Applied and environmental microbiology 72:4338-4346.
7. Dupont, K., F. K. Vogensen, H. Neve, J. Bresciani, and J. Josephsen. 2004. Identification of the receptor-binding protein in 936-species lactococcal bacteriophages. Applied and environmental microbiology 70:5818-5824.
8. Gasson, M. J. 1983. Plasmid complements of *Streptococcus lactis* NCDO 712 and other lactic streptococci after protoplast-induced curing. Journal of bacteriology 154:1-9.
9. Jarvis, A. W. 1984. Differentiation of Lactic Streptococcal Phages into Phage Species by DNA-DNA Homology. Applied and environmental microbiology 47:343-349.
10. Jarvis, A. W., V. R. Parker, and M. B. Bianchin. 1992. Isolation and characterization of 2 Temperate Phages from *Lactococcus lactis* ssp. *cremoris* C3. Can J Microbiol 38:398-404.
11. Josephsen, J., N. Andersen, H. Behrndt, E. Brandsborg, G. Christiansen, M. B. Hansen, S. Hansen, E. W. Nielsen, and F. K. Vogensen. 1994. An Ecological Study of Lytic Bacteriophages of *Lactococcus lactis* subsp. *cremoris* Isolated in a Cheese Plant over a Five Year Period. Int Dairy J 4:123-140.

12. Kampmann, M. L., S. L. Fordyce, M. C. Avila-Arcos, M. Rasmussen, E. Willerslev, L. P. Nielsen, and M. T. P. Gilbert. 2011. A simple method for the parallel deep sequencing of full influenza A genomes. J Virol Methods 178:243-248.
13. Koch, B., B. Christiansen, T. Evison, F. K. Vogensen, and K. Hammer. 1997. Construction of specific erythromycin resistance mutations in the temperate lactococcal bacteriophage TP901-1 and their use in studies of phage biology. Applied and environmental microbiology 63:2439-2441.
14. Kuipers, O. P., P. G. G. A. de Ruyter, M. Kleerebezem, and W. M. de Vos. 1998. Quorum sensing-controlled gene expression in lactic acid bacteria. J Biotechnol 64:15-21.
15. Lillehaug, D. 1997. An improved plaque assay for poor plaque-producing temperate lactococcal bacteriophages. J Appl Microbiol 83:85-90.
16. Lillehaug, D., B. H. Lindqvist, and N. K. Birkeland. 1991. Characterization of PhiLC3, a *Lactococcus lactis* subsp *cremoris* temperate bacteriophage with cohesive single-stranded DNA ends. Applied and environmental microbiology 57:3206-3211.
17. Mahony, J., H. Deveau, S. Mc Grath, M. Ventura, C. Canchaya, S. Moineau, G. F. Fitzgerald, and D. van Sinderen. 2006. Sequence and comparative genomic analysis of lactococcal bacteriophages jj50, 712 and P008: evolutionary insights into the 936 phage species. Fems Microbiol Lett 261:253-261.
18. Mahony, J., S. McGrath, G. F. Fitzgerald, and D. van Sinderen. 2008. Identification and characterization of lactococcal-prophage-carried superinfection exclusion genes. Applied and environmental microbiology 74:6206-6215.
19. Neve, H., A. Geis, and M. Teuber. 1984. Conjugal transfer and characterization of bacteriocin plasmids in group N (lactic acid) streptococci. Journal of bacteriology 157:833-838.
20. O'Driscoll, J., F. Glynn, O. Cahalane, M. O'Connell-Motherway, G. F. Fitzgerald, and D. Van Sinderen. 2004. Lactococcal plasmid pNP40 encodes a novel, temperature-sensitive restriction-modification system. Appl. Environ. Microbiol. 70:5546-5556.
21. Petersen, A., J. Josephsen, and M. G. Johnsen. 1999. TPW22, a lactococcal temperate phage with a site-specific integrase closely related to *Streptococcus thermophilus* phage integrases. Journal of bacteriology 181: 7034-7042.
22. Sambrook, J., E. F. Fritsch, and T. and Maniatis. 1989. Molecular cloning: a laboratory manual, 2 ed.
23. Sanders, M. E., and T. R. Klaenhammer. 1981. Evidence for Plasmid Linkage of Restriction and Modification in *Streptococcus cremoris* KH. Applied and environmental microbiology 42:944-950.
24. Schafer, A., A. Geis, H. Neve, and M. Teuber. 1991. Bacteriophage receptors of *Lactococcus lactis* subsp. 'diacetylactis' F7/2 and *Lactococcus lactis* subsp. *cremoris* Wg2-1. Fems Microbiol Lett 62:69-73.
25. Seegers, J. F., S. Mc Grath, M. O'Connell-Motherway, E. K. Arendt, M. van de Guchte, M. Creaven, G. F. Fitzgerald, and D. van Sinderen. 2004. Molecular and transcriptional analysis of the temperate lactococcal bacteriophage Tuc2009. Virology 329:40-52.
26. van Pijkeren, J. P., and R. A. Britton. 2012. High efficiency recombineering in lactic acid bacteria. Nucleic acids research 40:e76.
27. Van Pijkeren, J. P., K. M. Neoh, D. Sirias, A. S. Findley, and R. A. Britton. 2012. Exploring optimization parameters to increase ssDNA recombineering in *Lactococcus lactis* and *Lactobacillus reuteri*. Bioengineered 3:209-217.

The invention claimed is:

1. A method comprising:
   (i) providing a sample comprising at least one strain of *Lactococcus lactis* (*L. lactis*);
   (ii) performing a PCR analysis of the sample using at least a first primer pair adapted to generate a test amplicon correlating to a region of the cell wall polysaccharide (cwps) operon that is not conserved among strains of *L. lactis*, and using a control primer pair adapted to generate a control amplicon correlating to a region of the cwps operon that is conserved amongst strains of *L. lactis*; and
   (iii) detecting the presence or absence of the test amplicon in the strain of *L. lactis*, and
   (iv) detecting the presence of the control amplicon in the strain of *L. lactis*,
   wherein the test amplicon comprises a sequence selected from the group consisting of SEQ ID NOs: 9 to 11 and 13 to 15, and wherein the control amplicon comprises SEQ ID NO: 12.

2. The method according to claim 1, wherein the test amplicon is SEQ ID NO: 9 or SEQ ID NO: 13 and is a biomarker of phage sensitivity.

3. The method of claim 1, wherein the test amplicon detected is selected from SEQ ID NOS. 9 to 11 in the strain of *L. lactis*.

4. The method according to claim 1, wherein the test amplicon is SEQ ID NO: 10 or SEQ ID NO: 14 and is a biomarker of intermediate phage sensitivity.

5. The method according to claim 1, wherein the test amplicon is SEQ ID NO: 11 or SEQ ID NO: 15 and is a biomarker of phage insensitivity.

6. A method comprising:
   (i) providing a sample comprising at least one strain of *Lactococcus lactis* (*L. lactis*);
   (ii) performing a multiplex PCR analysis of the sample using
      (a) a first primer pair adapted to generate a first amplicon, wherein the first amplicon comprises SEQ ID NO: 9 or SEQ ID NO: 13;
      (b) a second primer pair adapted to generate a second amplicon, wherein the second amplicon comprises SEQ ID NO: 10 or SEQ ID NO: 14;
      (c) a third primer pair adapted to generate a third amplicon, wherein the third amplicon comprises SEQ ID NO: 11 or SEQ ID NO: 15; and (d) optionally, a control primer pair adapted to amplify a sequence conserved in *L. lactis*; and
(iii) detecting the presence or absence of the amplicons.

7. A method comprising:
(i) providing a sample comprising at least one strain of *Lactococcus lactis* (*L. lactis*);
(ii) performing a multiplex PCR analysis of the sample using
   (a) a first primer pair adapted to generate a first amplicon correlating to a region of the cwps operon, wherein the first primer pair comprises a forward primer comprising SEQ ID NO: 1 and a reverse primer comprising SEQ ID NO: 2;
   (b) a second primer pair adapted to generate a second amplicon correlating to a region of the cwps operon, wherein the second primer pair comprises a forward primer comprising SEQ ID NO: 3 and a reverse primer comprising SEQ ID NO: 4;
   (c) a third primer pair adapted to generate a third amplicon correlating to a region of the cwps operon, wherein the third primer pair comprises a forward primer comprising SEQ ID NO: 5 and a reverse primer comprising SEQ ID NO: 6; and
   (d) optionally, a control primer pair adapted to amplify a sequence conserved in *L. lactis*; and
(iii) detecting the presence or absence of the first, second and third amplicons wherein the presence of the first amplicon indicates the presence of a strain that is phage-sensitive, the presence of the third amplicon indicates the presence of a strain that is phage-insensitive, and the presence of the second amplicon indicates the presence of a strain having intermediate phage sensitivity.

8. The method according to claim 7 further comprising sub-typing the at least one strain of *L. lactis* as an MG-SK, an IL-KF, or a UC-CV sub-type.

9. The method according to claim 8, wherein the at least one strain is identified as phage-sensitive or MG-SK strain type, wherein one or more additional primer pairs are used to generate an amplicon selected from SEQ ID NOs: 26 to 30, and wherein the presence or absence of each amplicon is detected.

10. A method comprising:
(i) providing a sample comprising a mix of *Lactococcus lactis* (*L. lactis*) strains;
(ii) performing a multiplex PCR analysis of the sample using
   (a) a first primer pair adapted to generate a first amplicon correlating to a region of the cwps operon that is present in *L. lactis* strains MG1363 and SK11 but is not present in *L. lactis* strains IL1403, KF147, UC509.9 and CV56;
   (b) a second primer pair adapted to generate a second amplicon correlating to a region of the cwps operon that is present in *L. lactis* strains IL1403 and KF147 but is not present in *L. lactis* strains MG1363, SK11, UC509.9 and CV56;
   (c) a third primer pair adapted to generate a third amplicon correlating to a region of the cwps operon that is present in *L. lactis* strains UC509.9 and CV56 but is not present in *L. lactis* strains MG1363, SK11, IL403, and KF147; and
   (d) optionally, a control primer pair adapted to amplify a sequence conserved in *L. lactis*,
   wherein the PCR analysis provides a plurality of amplicons of different sizes; and
(iii) detecting the level of the first, second and/or third amplicons.

11. The method according to claim 10, wherein
(a) the first amplicon comprises or consists of SEQ ID NO: 9;
(b) the second amplicon comprises or consists of SEQ ID NO: 10; and
(c) the third amplicon comprises or consists of SEQ ID NO: 11.

12. The method according to claim 11, wherein the conserved sequence comprises all or part of the rmlB gene, and wherein the control primer pair optionally comprises a forward primer comprising SEQ ID NO: 7 and a reverse primer comprising SEQ ID NO: 8.

13. The method according to claim 11, further comprising at least two further primer pairs, wherein the at least two further primer pairs comprise a first further primer pair adapted to generate an amplicon selected from one of SEQ ID NOS: 26 to 30, and a second further primer pair adapted to generate an amplicon different from the first amplicon and selected from another of SEQ ID NOS: 26 to 30, wherein the primer pairs are used in separate amplifications.

14. The method according to claim 13, further comprising a third, a fourth and a fifth further primer pairs, each of which is adapted to generate a different amplicon from the first and second further primer pairs, wherein the amplicon is amplicons are selected from SEQ ID NOS: 26 to 30, and wherein the primer pairs are used in separate amplifications.

15. The method according to claim 10, wherein
(a) the first primer pair comprises a forward primer comprising SEQ ID NO: 1 and a reverse primer comprising SEQ ID NO: 2;
(b) the second primer pair comprises a forward primer comprising SEQ ID NO: 3 and a reverse primer comprising SEQ ID NO: 4; and
(c) the third primer pair comprises a forward primer comprising SEQ ID NO: 5 and a reverse primer comprising SEQ ID NO: 6.

\* \* \* \* \*

SEQUENCE LISTING

```
<160> NUMBER OF SEQ ID NOS: 30

<210> SEQ ID NO 1
<211> LENGTH: 23
<212> TYPE: DNA
<213> ORGANISM: Artificial Sequence
<220> FEATURE:
<223> OTHER INFORMATION: Forward primer for MG-SK cwps type

<400> SEQUENCE: 1
aaagctcatc tttcccctgt tgt                                      23

<210> SEQ ID NO 2
<211> LENGTH: 23
<212> TYPE: DNA
<213> ORGANISM: Artificial Sequence
<220> FEATURE:
<223> OTHER INFORMATION: Reverse primer for MG-SK cwps type

<400> SEQUENCE: 2
gcaccatagt ctggaataag acc                                      23

<210> SEQ ID NO 3
<211> LENGTH: 18
<212> TYPE: DNA
<213> ORGANISM: Artificial Sequence
<220> FEATURE:
<223> OTHER INFORMATION: Forward primer for IL-KF cwps type
```

<400> SEQUENCE: 3
gattcagttg cacggccg                                                                 18

<210> SEQ ID NO 4
<211> LENGTH: 19
<212> TYPE: DNA
<213> ORGANISM: Artificial Sequence
<220> FEATURE:
<223> OTHER INFORMATION: Reverse primer for IL-KF cwps type

<400> SEQUENCE: 4 agtaagggg cggattgtg                                                                 19

<210> SEQ ID NO 5
<211> LENGTH: 20
<212> TYPE: DNA
<213> ORGANISM: Artificial Sequence
<220> FEATURE:
<223> OTHER INFORMATION: Forward primer for UC-CV cwps type

<400> SEQUENCE: 5
gtgcctatgc tccgttagtc                                                               20

<210> SEQ ID NO 6
<211> LENGTH: 20
<212> TYPE: DNA
<213> ORGANISM: Artificial Sequence
<220> FEATURE:
<223> OTHER INFORMATION: Reverse primer for UC-CV cwps type

<400> SEQUENCE: 6
cgagggccaa tctctttacc                                                               20

<210> SEQ ID NO 7
<211> LENGTH: 28
<212> TYPE: DNA
<213> ORGANISM: Artificial Sequence
<220> FEATURE:
<223> OTHER INFORMATION: Forward primer for control cwps type

<400> SEQUENCE: 7
gtacactatg tttataacaa tcatccag                                                      28

<210> SEQ ID NO 8
<211> LENGTH: 25
<212> TYPE: DNA
<213> ORGANISM: Artificial Sequence
<220> FEATURE:
<223> OTHER INFORMATION: Reverse primer for control cwps type

<400> SEQUENCE: 8
gcaaaccaga ttcaaagtca gtatg                                                         25

<210> SEQ ID NO 9
<211> LENGTH: 686
<212> TYPE: DNA
<213> ORGANISM: Lactococcus lactis

<400> SEQUENCE: 9
aaagctcatc tttcccctgt tgtctatgta aacaatgtat caattcaaca aggaacaagt      60
acgaatacta caaaaatgaa tgttccaatt aaggctttca actccccaga caataatttt     120
ggaatgacgg cgaatgtgat ttctcagaca actggaactc agattacctc gtctgctccc     180
aaagtgaata cgactggtat aaattttgtt gaagtggatg caaataaaaa taagatggtt     240

```
agagatgctg tttatatttt agggaagaat gtgggtggta aaaagtatct atatgatagt        300
caagggaaat ggagcgaaat tcaagatttg tctacagttt ctcctacaag ctatacttta        360
ttaagaggtg ggaaccaata tgttttggt gatgatgatg tatctccaat tgagttgaat         420
aatacaagat tcaattatga ttatgaacgt gataccaaaa ttaatcaatc tttaatcaaa        480
ttatttggtt tgggagaagg aaaagattat ttcctttatc aggttgccgc tcctactaac        540
tactctgttg ataaaacacc cattgatttt tctattttt cagaaaatgt agtttcgcct         600
aatggtagcc aacttactaa aactagtatg aagacagcaa gcaaccaatc atttaaacta        660
aatggtctta ttccagacta tggtgc                                            686
```

```
<210> SEQ ID NO 10
<211> LENGTH: 183
<212> TYPE: DNA
<213> ORGANISM: Lactococcus lactis

<400> SEQUENCE: 10
gattcagttg cacggccgta tgaaactcat caagttaatt ttgatagtac gatgacactt        60
ctcgagatct tacgtcaaaa taaaaaatca ttgaaacgat ttgttttttc ttcaagcgca        120
gcagtttatg gtgatgagcc aacacttcct aagcaggaag agggcacaat ccgccccctt       180
act                                                                     183
```

```
<210> SEQ ID NO 11
<211> LENGTH: 442
<212> TYPE: DNA
<213> ORGANISM: Lactococcus lactis

<400> SEQUENCE: 11
gtgcctatgc tccgttagtc tttgatcatg aaatccaaat ttccccaaca gcaagtgata        60
cattgaaaat gattaatttt cctaaaaaac caggaattta ttctgaaaat ctaactggga       120
tttcaagttg tctggttgta aagagcgact tattaataga aattggcgga ctgaatattg       180
aatttccctt agattatctt gaccattggc tattttggaa attttttaat tctaataaaa       240
aggtagtagt aattaatgaa aaaataaatc accatctttc tattcaagaa ataaatcaaa       300
caaatgatct gagattttat agtatcttct ctagtgaata tcattttat aagtattata       360 agccggaatt gctcttaaat ctttataaaa aatatgttag aatgattatt aaaggaattc       420
ttggtaaaga gattggccct cg                                                442
```

```
<210> SEQ ID NO 12
<211> LENGTH: 889
<212> TYPE: DNA
<213> ORGANISM: Lactococcus lactis

<400> SEQUENCE: 12
gtacactatg tttataacaa tcatccagac gtgcatatca cagttttgga taaattaact        60
tatgcaggaa atgttaataa cattaacatg ttatttgaca gtggacgtgt cgaacttgtt       120
gttggcgaca ttgcagaccc tgaaattgtt gatcaagtgg cttctaaagc agatgcaatt       180
gttcactatg cagctgagag ccataatgat aattcattga atctcaagaa tgaatttata       240 caaacaaaact ttatcggaac ttatacgttg attcaagcgg ctcgtaaata tgatttacgt       300
ttccaccatg tttctactga tgaagtttat ggtgatttgc cttatcgcga agatttgcca       360
ggccatggcg aaggtgaagg tgaaaaattt actgacaaaa caccttacaa tccatcaagc       420
```

```
cctactctt caactaaagc ggcttctgat ttaattgttc gtgcttgggt acgttcattt      480
ggacttaaag caacaatttc aaactgctca ataactacg gacctttca acacatcgaa       540 aaatttattc ctcgtcaaat tactaatatt ctttcaggaa tcaaaccaaa actttacggt     600
gatggtaaaa acgttcgaga ctggattcat acagacgacc attcatcagg cgtttggaca    660
attttgaata aggtcgtat gggtgaaact taccttatcg gtgcagacgg tgaaaaaaat     720
aacaaagaag ttcttgaaga tattttgact cgtatgggca agataagag cgattatgat    780 cgtgtaactg accgtgctgg ccatgacctt cggtacgcaa ttgacaatac aaaattgcgt    840
accgaacttg gttgggctcc aaaacatact gactttgaat ctggtttgc                889
```

<210> SEQ ID NO 13
<211> LENGTH: 1419
<212> TYPE: DNA
<213> ORGANISM: Lactococcus lactis

<400> SEQUENCE: 13

```
ttgaaagtat taaaaaacta tcttctgaat agctcttacc aattattgat tgtgattatt    60
ccaattatca cgattcctta tatttctagg gtgcttggca aacggctat aggttaaat   120 acatttacct atgcaattat tcagtacttt gtattagctg gttcaattgg ataacaact   180 tatggaaatc gagagattgc atatcatcaa tctgataaag aaaagagaag ccaaattttt   240
tgggaaattt cattttgag attttgtacc attgctctct cttttcttat ttctgtatt   300 ttcttagcct ttcaaaaaca ggattttgag atttatctct tgcagagtat cgctattatc    360
gctgcggctt ttgatatttc ttggtatttt atgggagtgg aaaatttcaa gcgaacagta    420
gggcgtaatt ttattgtctc tattatttca gttattttca tctttacttt tattaagagt    480 ccaaggatt tgcccattta tgttttaatc attactggaa catcattgat tggaaatctt     540
tcactttggc catatttgcg caaggaaatt ttcgctccca atggaaaga attagcatta    600 ggacatcatt taaaacccac actattactt ttttgccgc aaattgctac acagatttat    660
acaattgcaa acaaaacgat gattgggatt tttgatggga aaacggcatc gggattttt    720 agtcaatcgg atagtctgat taagtaaca ttgagcattg tcacttcttt aggtgtagtc     780
atgttgcctc atgtttcaaa tcttttttca aaaggtaaaa ttaagaagt tcaagagact    840 ttaaaaaaat ctttcgtcct tatgactggg cttgctgtac cgataatgtt tggcgttatg    900
ggaatagcac tcaattttgc aggattcttt ttcggcccta atgggtagc tgttggtcct    960 ttgctaatga tggaagcccc aattattata ttcattgctt ggagtaatgt tttgggaatt    1020
cagtaccttc ttccattaaa tcggatgaga gaattcacaa cttcggtaac aattggtgca    1080
gttcttaata ttttactaa ttttgctttg attcctcttt tggggctcac tggtgcaatg    1140
attgcgacag taattgccga ggcttcagtg acgatttatc aatttttatat tttgagaaat    1200 gactttgaga taattccaat gattttatct tgctggaaat actttttatc tggtgcagtg    1260
atgtttggag ctgttttcta tttaaacaat tctttgaaga tgaatatgca taatcttata    1320
tttcaagtat tgattggtgc tataatatat ataattctta atatcttatt gaaatccagt    1380
ctttttattg aagtcaaaaa gattgtaagt aaaaaataa                           1419
```

<210> SEQ ID NO 14
<211> LENGTH: 942
<212> TYPE: DNA
<213> ORGANISM: Lactococcus lactis

<400> SEQUENCE: 14

```
atgataacaa agagtaacat actaataaca ggtggagcag gttttattgg ctcaagttta      60
gcgaacgaat tactacctca aaataagatt actgttattg ataatctttc gatgggagat     120
tttaataatc ttcatgaaac aagtaatctt acaaaaattt taggtgatgt cactgataaa     180
aatctcctgg taaaagtttt ggaagaaaat gattttgatt atattttca tttagcagca      240 attgcttcgg ttgccgattc agttgcacgg ccgtatgaaa ctcatcaagt taattttgat    300
agtacgatga cacttctcga gatcttacgt caaaataaaa aatcattgaa acgatttgtt    360 tttcttcaa gcgcagcagt ttatggtgat gagccaacac ttcctaagca ggaagagggc     420
acaatccgcc cccttactcc ttatgcaatt gataaatttg catctgaaaa aatgacaatg    480
atttataata atttatatga tgttcctacc agtgcaacac gcttttcaa tgtttatgga     540 ccaaatcaaa atcccagttc accctattca ggatttattt ccattcttgt tgaccgtttg    600
cgagaaaata cagaattgac tattttttgga gatggagaac agtctcgaga ttttgtatat  660
atagaagatg ttattcaagc attattacta atagcgacct ctgaacaatc ctttggagaa    720
gtctataatg tcgggactgg ggtcaaaaat tcaataaacg atttaacgaa atttgctcaa    780
aaatttacaa ataagagtt atctatcaaa tttgatgatg tgcgacaagg agatatcaaa     840
gactcagttt ccgatatttc aaaacttaag gacataggat actcacctaa atttgattta    900
tctaatggta tgaagaagta tctcaactac gagtttaaat aa                       942

<210> SEQ ID NO 15
<211> LENGTH: 837
<212> TYPE: DNA
<213> ORGANISM: Lactococcus lactis

<400> SEQUENCE: 15
atgaatttaa caatttgctt agtagcttat agtcaaaaat ttacagagac agtctcattt      60
tattctttat taaacttgac taagaatcta aagaaaata ttaatttata tatttttgac     120
aatggaagtg aagatttttc gtcctctcat gaggagttgg atactcattc atttcatagc    180
ttgaactata tttataataa acaaaagaa cgtggtacta gaattgctta tcaaagtatt    240
ttagatgtta gtcaagatga atggttaatg tttttagacg atgatacaga aatttcacaa    300
ccatatttat cgaaaatttt atcagaaata aaaaagaaa accaaagtga tatttgtgcc    360
tatgctccgt tagtctttga tcatgaaatc caaatttccc caacagcaag tgatacattg    420
aaaatgatta attttcctaa aaaaccagga atttattctg aaaatctaac tgggatttca    480
agttgtctgg ttgtaaagag cgacttatta atagaaattg gcggactgaa tattgaattt    540
cccttagatt atcttgacca ttggctattt tggaaaattt ttaattctaa taaaaaggta    600
gtagtaatta atgaaaaaat aaatcaccat ctttctattc aagaaataaa tcaaacaaat    660
gatctgagat tttatagtat cttctctagt gaatatcatt tttataagta ttataagccg    720
gaattgctct taaatctta taaaaatat gttagaatga ttattaaagg aattcttggt     780
aaagagattg gccctcgttg gaaaattta ttaaaaatat tattggagag aaaatga        837

<210> SEQ ID NO 16
<211> LENGTH: 21
<212> TYPE: DNA
<213> ORGANISM: Artificial Sequence
<220> FEATURE:
<223> OTHER INFORMATION: Primer

<400> SEQUENCE: 16
```
gtcatcaaac atactttcgt c                                           21

<210> SEQ ID NO 17
<211> LENGTH: 21
<212> TYPE: DNA
<213> ORGANISM: Artificial Sequence
<220> FEATURE:
<223> OTHER INFORMATION: Primer

<400> SEQUENCE: 17
aagttttgcc attgtttctc c                                           21

<210> SEQ ID NO 18
<211> LENGTH: 23
<212> TYPE: DNA
<213> ORGANISM: Artificial Sequence
<220> FEATURE:
<223> OTHER INFORMATION: Primre

<400> SEQUENCE: 18
gaacaatgga ttatttatgc tga                                         23

<210> SEQ ID NO 19
<211> LENGTH: 21
<212> TYPE: DNA
<213> ORGANISM: Artificial Sequence
<220> FEATURE:
<223> OTHER INFORMATION: Primer

<400> SEQUENCE: 19
attcccattt tcagcaacaa g                                           21

<210> SEQ ID NO 20
<211> LENGTH: 21
<212> TYPE: DNA
<213> ORGANISM: Artificial Sequence
<220> FEATURE:
<223> OTHER INFORMATION: Primer

<400> SEQUENCE: 20
gttgtaattg ttactagcca g                                           21

<210> SEQ ID NO 21
<211> LENGTH: 23
<212> TYPE: DNA
<213> ORGANISM: Artificial Sequence
<220> FEATURE:
<223> OTHER INFORMATION: Primer

<400> SEQUENCE: 21
tcaatcgcat tatagattac acc                                         23

<210> SEQ ID NO 22
<211> LENGTH: 21
<212> TYPE: DNA
<213> ORGANISM: Artificial Sequence
<220> FEATURE:
<223> OTHER INFORMATION: Primer

<400> SEQUENCE: 22
gattttattc gaggcttagc a                                           21

<210> SEQ ID NO 23
<211> LENGTH: 22
<212> TYPE: DNA
<213> ORGANISM: Artificial Sequence

```
<220> FEATURE:
<223> OTHER INFORMATION: Primer

<400> SEQUENCE: 23
tagcattaca atcaatctgt ca                                              22

<210> SEQ ID NO 24
<211> LENGTH: 21
<212> TYPE: DNA
<213> ORGANISM: Artificial Sequence
<220> FEATURE:
<223> OTHER INFORMATION: Primer

<400> SEQUENCE: 24
gattatattc ggggcttagc a                                               21

<210> SEQ ID NO 25
<211> LENGTH: 22
<212> TYPE: DNA
<213> ORGANISM: Artificial Sequence
<220> FEATURE:
<223> OTHER INFORMATION: Primer

<400> SEQUENCE: 25
tgtaatatgg tattgtctag ca                                              22

<210> SEQ ID NO 26
<211> LENGTH: 743
<212> TYPE: DNA
<213> ORGANISM: Lactococcus lactis

<400> SEQUENCE: 26
gtcatcaaac atactttcgt catatgtgcg tatatgcaat ctccgtattt agaggaaagt      60
ataaaatcaa ttttagacca aggatctatt aaagaaggaa atcagaagtg gttttatata    120
cttctactcc taatgattat atagaaaata tttgtcataa atataatatc aaaatattta    180
ttggtgaagg tggaggcatt ggagcagatt ggaatggagc tttagcggca gttcaaacta    240
aatatgctac aattgttcat caagacgatc tatatgataa gaaatatgga gaaatgataa    300
ttaatgattt tgagtctcaa aaagactcta atattgtttt tactgactat tatgaaattg    360
atgaatactc taaacctaga aaagaaata ttaatttaaa aataaaaagt ttaggattaa    420
aactaatgtc ttttttgggaa aataaaaaat atcaaagaag agtttactct tttggtaatt    480
ttatttgttg cccagctgtt tcttataata tggaacgtct taaagatttt agatttaatg    540
aagagatgaa aatggcggta gactgggatg catgggaaag aataatgaaa aaatctggac    600
atgtccatta tcttccgcta aaattgatgg ctcatagaat acatagtgat tcggaaacaa    660
ccaataatac tttaaataaa aacagagaaa aagaagagca cgagatgttt cgaagatatt    720
ggggagaaac aatggcaaaa ctt                                            743

<210> SEQ ID NO 27
<211> LENGTH: 651
<212> TYPE: DNA
<213> ORGANISM: Lactococcus lactis

<400> SEQUENCE: 27
gaacaatgga ttatttatgc tgaaaaatta aagcaaatgt ttcctgaaat gaaattaata     60
gggtggctgc atctggatct caaccattat gaaacttatc atcttgcgaa agcaaaaat    120 caatttttaa atggtcttag ggtgtgtgat cggttgattg tactaactca agaggaaaaa    180
```

| | |
|---|---:|
| aatgttctag aaaaccgcgg atttgaaaaa gttcaagttt tgcataatcc acttacatta | 240 |
| aatgatacaa ataagttgt ggacttgaat aaaaaaataa tatcatgggt aggacggatt | 300 |
| gatattttgc ataagggctt ggactattta atagagatag cgaaaatttt gcctgacgac | 360 |
| tgggaaatta gagtagctgg ttccggaagg gacaacaaaa gatttaaaaa attgattgaa | 420 |
| aaaaatagge ttacgaataa aattttatgg gtaggtccga aaatggaga agaactaaca | 480 |
| tatcattatt taaatagctc cattttttta atgacatcaa gatttgaaag ctttggctta | 540 |
| gtattggtag aagcaatgaa ctatggtctt cctataattg cattctcaca aacaggaagt | 600 |
| gatgaaattc ttaaaaatga acaatatggc cttgttgctg aaaatgggaa t | 651 |

<210> SEQ ID NO 28
<211> LENGTH: 449
<212> TYPE: DNA
<213> ORGANISM: Lactococcus lactis

<400> SEQUENCE: 28

| | |
|---|---:|
| gttgtaattg ttactagcca gcatgataaa gacttgccta ctaaagaaga atttgatcat | 60 |
| ttgaaaatat atcggttgcc tattagaaag atttggaaaa atcggtatcc ttttccatta | 120 |
| aaaaatgaaa gatataaaca attaatttct gatattactt ctgaaccaat tgactattat | 180 |
| gtagtgaata caagatttca attgcctgct ttattaggtg cccagttagc aaaaaaagca | 240 |
| ggaaaagaag ccttggtatt agagcatggg accacgtacc tcacattaaa taattctttg | 300 |
| ttagatagca tacttcacag gatagagcac ttttggtta aaaaaatcaa aaaaaatact | 360 |
| aagactttt acggtgtttc aaaagaagct actgaatggt taaagacttt tggaatagag | 420 |
| gctaaaggtg taatctataa tgcgattga | 449 |

<210> SEQ ID NO 29
<211> LENGTH: 968
<212> TYPE: DNA
<213> ORGANISM: Lactococcus lactis

<400> SEQUENCE: 29

| | |
|---|---:|
| gattttattc gaggcttagc aaagaaaatt ttaacataga aagagtattt ttataaatga | 60 |
| gtgaaaagaa atatgattcg gagactttgg aacgacttca agagatacta cgaatgatgt | 120 |
| tagcagattt tgataaaata tgctaagata acgatattga ttattttta atgggtggaa | 180 |
| gtttacttgg agctgtaagg cacaatggga tgataccttg ggatgatgat attgacgttg | 240 |
| gaatgactgg tgagaattat gataaattta tacaagtcat gaataattca caaaatgaaa | 300 |
| aatatagtct tatgagtagt gagagcgagg aaagctatac cactcagatt gtactggata | 360 |
| ttttagcatt tgacaatcta gcagataatg aaagacgtgc aaaaattcaa ggtataaaat | 420 |
| ctttcatata tgggaaactt tcatatctta caacaattga aaaccctaca gttcatcaag | 480 |
| taggaataaa actattttt attaatacta caataaaaag tctttcaaaa acattcaaa | 540 |
| cttttaaag ttaccctaa attttttatt aaaaaggtg aaggagtagc tagaaaatat | 600 |
| aactcttctc aaacgcaaag agtaatgtat atgaatcagt caaaaatgtt ttcagaaatt | 660 |
| tttgatcgaa atgacctctt accaactaga cgtgttgatt ttgatggaca aaaaataaaa | 720 |
| attccaaagg aaacagataa atatttggct gcacattatg gtgattatat gacacttcca | 780 |
| ccagaagata aaagatataa tcattatacg gccattttag attttggaaa gtataaataa | 840 |
| ggtaaaatat aatgaaagat aaagaaaaaa ttgtattggt tgctggaact tttgatattt | 900 |
| tgcatgagag ccacgttaat atgttgaaaa atgctaaaaa tcttggtgac agattgattg | 960 |

```
<210> SEQ ID NO 30
<211> LENGTH: 1141
<212> TYPE: DNA
<213> ORGANISM: Lactococcus lactis

<400> SEQUENCE: 30
gattatattc ggggcttagc aaagaaaatt ttaacataga aagagtatt    ttataaatga      60 gtgaaaagaa atatgattcg gagactttag aaggacttca agagatacta cgaatgatgt     120
tagcagattt tgataaaata tgcgaagata acgatattga ttatttttta gtaggtggaa     180
gtttacttgg agcgataagg cacaatggga tgataccttg ggatgatgac attgacattg     240
gtatgaccgg aaaagattat gataaattta ttcaaatcat gaagaagagg gaatctgata     300
aatatacgct tataagtagt gaaacaaata aagaatttcc atatttgcga tctgcgggat     360
ttatgctaaa tggtacaaaa tttataaaag atatttcaat aatggatgaa acctcttcta     420
gtatagtagt tgacattatt gcgttcgata acttagcaga tggtaagtta aaaagcatct     480
cacaaggctt aaaaacattt ttctacggta aatctgcctt ccttacaact ctgaataatc     540
ctacgaatca taggaaagga atttcaaaaa ttgttacgac agttatgata aaaatgctcc     600
atggattatt taagttattt aaagtaaccc cacatttctt cattaacaaa ggaaacaaaa     660
tagcaacgaa atataatatg ctggaaacag gaagagtcat gtacatgaat gaatctaaac     720 cgttttagt  tacaattaag aagaaaaatt tatttcccat aaagaaaatt ccttttgatg     780
gcttgatgat tagtgtccca aataacccag aacagtattt attagaaaga tatggagatt     840
ataagacact accgccagaa agtgagcaat ataatcattt cccagatgta ttggactttg     900
gagaatacaa aaatttaagg agaagagagc aatgaaatta gcattattga cggctggagg     960
agttggtagc cgtatgaaac aagaggtacc taaacagttt attcatgtaa atgataaacc    1020
tttaatcatt tatgctttag aggcttttca aaagcatcca gatattgatg taattgctat    1080
tgcatgctta gaaggatgga aaaatgttt  ggaggcatat gctagacaat accatattac    1140
a                                                                    1141
```